(12) United States Patent
Itagaki et al.

(10) Patent No.: US 10,238,589 B2
(45) Date of Patent: *Mar. 26, 2019

(54) SILICON OXIDE-COATED ZINC OXIDE, METHOD FOR PRODUCING SAME, AND COMPOSITION AND COSMETIC INCLUDING SILICON OXIDE-COATED ZINC OXIDE

(71) Applicant: Sumitomo Osaka Cement Co., Ltd, Tokyo (JP)

(72) Inventors: Tetsuro Itagaki, Tokyo (JP); Gaku Fujihashi, Tokyo (JP); Syunsuke Suma, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/126,140

(22) PCT Filed: Mar. 30, 2015

(86) PCT No.: PCT/JP2015/059878
§ 371 (c)(1),
(2) Date: Sep. 14, 2016

(87) PCT Pub. No.: WO2015/152138
PCT Pub. Date: Oct. 8, 2015

(65) Prior Publication Data
US 2017/0095407 A1 Apr. 6, 2017

(30) Foreign Application Priority Data

Mar. 31, 2014 (JP) ................. 2014-073128
Mar. 31, 2014 (JP) ................. 2014-073129

(51) Int. Cl.
| A61K 8/27 | (2006.01) |
| A61K 8/25 | (2006.01) |
| A61K 8/02 | (2006.01) |
| C09C 1/04 | (2006.01) |
| A61Q 17/04 | (2006.01) |

(52) U.S. Cl.
CPC ............. *A61K 8/27* (2013.01); *A61K 8/0241* (2013.01); *A61K 8/25* (2013.01); *A61Q 17/04* (2013.01); *C09C 1/043* (2013.01); *A61K 2800/412* (2013.01); *A61K 2800/413* (2013.01); *A61K 2800/621* (2013.01); *C01P 2002/82* (2013.01); *C01P 2002/86* (2013.01); *C01P 2004/62* (2013.01); *C01P 2004/64* (2013.01); *C01P 2004/84* (2013.01); *C01P 2006/22* (2013.01)

(58) Field of Classification Search
None
See application file for complete search history.

(56) References Cited

U.S. PATENT DOCUMENTS

| 5,468,289 | A | * | 11/1995 | Herget | ................. | C09C 1/0015 |
| | | | | | | 106/31.88 |
| 6,087,059 | A | * | 7/2000 | Duggan | ............. | G03G 9/09708 |
| | | | | | | 430/108.22 |
| 6,132,743 | A | | 10/2000 | Kuroda et al. | | |
| 6,528,034 | B1 | * | 3/2003 | Pinnavaia | ............... | C01B 37/02 |
| | | | | | | 423/335 |
| 6,534,044 | B1 | * | 3/2003 | Wada | .................. | A61K 8/0212 |
| | | | | | | 106/436 |
| 6,660,380 | B1 | * | 12/2003 | Ishida | ..................... | A61K 8/11 |
| | | | | | | 427/215 |
| 2005/0090634 | A1 | * | 4/2005 | Morse | ..................... | B01J 21/08 |
| | | | | | | 528/12 |
| 2006/0167138 | A1 | | 7/2006 | Ishii et al. | | |
| 2008/0070140 | A1 | * | 3/2008 | Fomitchev | .............. | C09C 3/041 |
| | | | | | | 430/108.3 |
| 2010/0003202 | A1 | * | 1/2010 | Matsumoto | ............ | A61K 8/027 |
| | | | | | | 424/59 |
| 2010/0233103 | A1 | * | 9/2010 | Shirao | ...................... | A61K 8/06 |
| | | | | | | 424/59 |
| 2011/0226990 | A1 | * | 9/2011 | Glennon | ................ | B01J 20/283 |
| | | | | | | 252/184 |

FOREIGN PATENT DOCUMENTS

| EP | 2995590 A1 | 3/2016 |
| EP | 3070054 A1 | 9/2016 |

(Continued)

OTHER PUBLICATIONS

Parler et al. Journal of Non-Crystalline Solids 2001 279:119-125.*
Faure et al. Science and Technology of Advanced Materials 2013 14:1-23 (Year: 2013).*
Liz-Marzan et al. Langmuir 1996 12:4329-4335 (Year: 1996).*
International Search Report of PCT/JP2015/059878 dated Jun. 30, 2015.
International Search Report of PCT/JP2014/059503 dated Jun. 24, 2014.
Grasset et al., "Surface modification of zinc oxide nanoparticles by aminopropyltriethoxysilane," Journal of Alloys and Compounds, 360:298-311 (2003).
Casu et al., Journal of Non-Crystalline Solids, 315:97-106 (2003).
Yabuki et al., Physical Chemistry Chemical Physics, 4:4830-4837 (2002).
Belton et al., "An overview of the fundamentals of the chemistry of silica with relevance to biosilicification and technological advances: Fundamentals of silica chemistry," FEBS Journal, 279(10):1710-1720 (2012).
Search Report for European Patent Application No. 15772843.7 (dated Aug. 9, 2017).

*Primary Examiner* — Robert A Wax
*Assistant Examiner* — Caralynne E Helm
(74) *Attorney, Agent, or Firm* — Merchant & Gould P.C.

(57) ABSTRACT

Provided are a silicon oxide-coated zinc oxide, a method for producing the same, a composition and a cosmetic including a silicon oxide-coated zinc oxide. The silicon oxide-coated zinc oxide is a silicon oxide-coated zinc oxide formed by coating surfaces of zinc oxide particles with a silicon oxide coat, in which an average particle diameter of the zinc oxide particles is in a range of more than 50 nm and 500 nm or less, and, when an abundance ratio of silicon in the silicon oxide coat in a $Q^3$ environment is indicated by $Q^3$, and an abundance ratio in a $Q^4$ environment is indicated by $Q^4$, $Q^3+Q^4 \geq 0.6$ and $Q^4/(Q^3+Q^4) \geq 0.5$ are satisfied.

9 Claims, 3 Drawing Sheets

(56) References Cited

FOREIGN PATENT DOCUMENTS

| | | |
|---|---|---|
| JP | H08-59238 A | 3/1996 |
| JP | 2851885 B2 | 1/1999 |
| JP | H11302015 A | 11/1999 |
| JP | 3187440 B2 | 7/2001 |
| JP | 2002-308716 A | 10/2002 |
| JP | 2004059421 A | 2/2004 |
| JP | 2007016111 A | 1/2007 |
| JP | 2007197412 A | 8/2007 |
| JP | 2007-525396 A | 9/2007 |
| JP | 2008-266283 A | 11/2008 |
| JP | 2008-280465 A | 11/2008 |
| JP | 4582439 B2 | 11/2010 |
| JP | 2014043376 A | 3/2014 |
| WO | 98/17730 A1 | 4/1998 |
| WO | 2006/105600 A1 | 10/2006 |

* cited by examiner

SILICON OXIDE-COATED ZINC OXIDE, METHOD FOR PRODUCING SAME, AND COMPOSITION AND COSMETIC INCLUDING SILICON OXIDE-COATED ZINC OXIDE

TECHNICAL FIELD

The present invention relates to a silicon oxide-coated zinc oxide, a method for producing the same, and a composition and a cosmetic including a silicon oxide-coated zinc oxide. In more detail, the present invention particularly relates to a silicon oxide-coated zinc oxide that is preferably used for facial lotions, sunscreen gels, emulsions, creams, foundations, lipsticks, rouge, eyeshadows, and the like which require an ultraviolet ray-screening function, a method for producing the same, and a composition and a cosmetic including a silicon oxide-coated zinc oxide.

The present application claims priority on the basis of Japanese Patent Application No. 2014-73128, filed on Mar. 31, 2014 and Japanese Patent Application No. 2014-73129, filed on Mar. 31, 2014, the contents of which are incorporated herein by reference.

BACKGROUND ART

Ultraviolet radiation has become a cause of the deterioration of a number of materials such as a resin and rubber and is said to, for human beings, possibly act as a cause of not only sun tanning or sunburn but also an aging phenomenon or skin cancer. Therefore, an ultraviolet ray-screening agent is widely used in the fields of films, paints, cosmetics, and the like.

As the ultraviolet ray-screening agent, organic ultraviolet ray-screening agents such as a benzophenone-based ultraviolet ray-screening agent, a methoxycinnamic acid-based ultraviolet ray-screening agent, and a dibenzoylmethane-based ultraviolet ray-screening agent or inorganic ultraviolet ray-screening agents such as zinc oxide and titanium oxide are generally used.

The organic ultraviolet ray-screening agents have problems in that there is a concern that the organic ultraviolet ray-screening agents may deteriorate due to heat or the prolonged exposure to ultraviolet radiation, and a single kind of organic ultraviolet ray-screening agent is not capable of absorbing ultraviolet rays in a wide range and thus it is necessary to use a combination of multiple kinds of organic ultraviolet ray-screening agent having different ultraviolet ray absorption wavelengths.

On the other hand, the inorganic ultraviolet ray-screening agents have an effect of absorbing ultraviolet rays having wavelengths that correspond to the band gaps of inorganic particles included in the inorganic ultraviolet ray-screening agent and advantages that the inorganic ultraviolet ray-screening agents do not deteriorate due to heat or the prolonged exposure to ultraviolet radiation, have excellent weather resistance, heat resistance, and the like, and are capable of screening ultraviolet rays in a wide wavelength range since the inorganic ultraviolet ray-screening agents screen ultraviolet rays through scattering attributed to the refractive index of the inorganic particles.

By the way, since the inorganic ultraviolet ray-screening agents scatter not only ultraviolet rays but also visible light rays, even the inorganic ultraviolet ray-screening agents having the above-described advantages have a problem in that the skin easily becomes whitish when a large amount of the inorganic ultraviolet ray-screening agent is blended into cosmetics or the like. Therefore, in order to cope with the above-described problem, an appropriate combination of the inorganic ultraviolet ray-screening agent and the organic ultraviolet ray-screening agent is used.

As the inorganic ultraviolet ray-screening agent, titanium oxide, zinc oxide, and the like are generally used. Particularly, zinc oxide is capable of screening ultraviolet rays in a wide wavelength range from the UV-A region (320 nm or more and 400 nm or less) to the UV-B region (280 nm or more and 320 nm or less).

For example, when zinc oxide and titanium oxide are compared with each other in terms of the photocatalytic activity through which a substance in contact with the surfaces of particles is oxidized, zinc oxide has extremely lower photocatalytic activity. In addition, the refractive index of zinc oxide is 2.0, which is lower than the refractive index of titanium oxide (2.7), and thus, in a case in which zinc oxide is made into nanoparticles, the zinc oxide particles have excellent transparency. As a result, zinc oxide has been attracting attention as an ultraviolet ray-screening agent.

Meanwhile, since zinc is an ampholytic element, zinc oxide, which is an oxide of zinc, has characteristics of easily dissolving in an acid and an alkali, in addition, slightly dissolving in water as well, and releasing zinc ions, and these characteristics prevent zinc from becoming a sufficiently stable element.

In addition, while zinc oxide has an extremely lower photocatalytic activity compared with titanium oxide, the photocatalytic activity is desirably suppressed. For example, in a case in which zinc oxide is made into nanoparticles so that the average particle diameter thereof reaches 50 nm or less, the specific surface area is increased and thus the photocatalytic activity becomes high.

As described above, zinc oxide particles have particularly significant problems of the release of zinc ions and a high photocatalytic activity.

In addition, compared with oil-based cosmetic products, water-based cosmetic products are not sticky and are capable of obtaining a fresh feeling during use, and thus, in recent years, the water-based cosmetic products have been used as a variety of cosmetics such as sunscreens, emulsions, and creams. In a case in which zinc oxide is used for the water-based cosmetic, zinc ions being eluted react with a water-soluble macromolecule of an organic ultraviolet ray-screening agent or a viscosity improver, and there is a concern that problems of the degradation of performance as cosmetics, discoloration, a change in the viscosity, and the like may be caused. Therefore, there has been a problem in that the degree of freedom in formulation is limited.

For example, when a carbomer (carboxyvinyl polymer), which is generally used as a viscosity improver, and zinc oxide are jointly used, a zinc ion being eluted and a carboxylate group (COO—) of the carbomer react with each other, and thus the gel structure of the carbomer breaks, and there is a problem in that the viscosity decreases.

As described above, in order to solve the problems of zinc oxide, there have been a variety of proposals regarding zinc oxide coated with an inorganic oxide.

For example, there has been a proposal regarding a method in which zinc oxide is added to an aqueous solution of silicate of soda so as to be brought into a suspended state, and then the hydrogen-ion exponent (pH) is held at approximately 7, thereby obtaining silica-coated zinc oxide (Patent Literature No. 1).

In addition, there has been a proposal regarding a method in which zinc oxide, which is a raw material, is brought into contact with a composition for forming a silica coat containing silicic acid or a precursor capable of generating silicic acid, which does not contain an organic group and a halogen, water, an alkali, and an organic solvent, thereby obtaining silica-coated zinc oxide which does not deteriorate by weather due to the photocatalytic activity (Patent Literature No. 2).

In addition, there has been a proposal regarding a method in which zinc oxide powder is coated with at least one of organopolysiloxanes and silicone compounds (excluding silane compounds) in a non-gaseous state, and is calcinated at a temperature in a range of 600° C. or higher and 950° C. or lower in an oxidizing atmosphere, thereby obtaining activity-suppressing zinc oxide powder coated with silicon oxide (Patent Literature No. 3).

CITATION LIST

Patent Literature

[Patent Literature No. 1] Japanese Patent No. 2851885
[Patent Literature No. 2] Japanese Patent No. 4582439
[Patent Literature No. 3] Japanese Patent No. 3187440

SUMMARY OF INVENTION

Problems to be Solved by the Invention

However, in the methods described in Patent Literature Nos. 1 to 3, there have been no studies regarding the elution of zinc ions, and there has been a problem in that it is difficult to sufficiently suppress the release of zinc ions from zinc oxide even when zinc oxide is coated with silica.

In addition, in order to obtain highly transparent cosmetics, zinc oxide having an average particle diameter of 50 nm or less is preferably used, but there is a problem in that, in a case in which zinc oxide is pulverized so as to have an average particle diameter of 50 nm or less, compared with zinc oxide particles having an average particle diameter of more than 50 nm, the ultraviolet ray-scattering effect degrades, and the capability of screening rays having a long wavelength, particularly, ultraviolet rays (UV-A) having a long wavelength, is poor.

The present invention has been made in consideration of the above-described circumstances, and an object of the present invention is to provide a silicon oxide-coated zinc oxide capable of suppressing the elution of zinc ions from zinc oxide particles, a method for producing the same, and a composition and a cosmetic including a silicon oxide-coated zinc oxide.

Means for Solving the Problems

As a result of repeating intensive studies in order to solve the above-described problems, the present inventors found that, in a silicon oxide-coated zinc oxide formed by coating the surfaces of zinc oxide particles having an average particle diameter in a range of more than 50 nm and 500 nm or less with a silicon oxide coat, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, the silicon oxide coat is capable of inhibiting the elution of zinc ions from the zinc oxide particles and found that, when this silicon oxide-coated zinc oxide is applied to cosmetics, zinc ions are not eluted, and thus problems attributed to the elution of zinc ions are solved, furthermore, the ultraviolet ray-screening function improves, and the transparency is also excellent, and thus the present inventors completed the present invention.

That is, a silicon oxide-coated zinc oxide of the present invention is a silicon oxide-coated zinc oxide formed by coating surfaces of zinc oxide particles with a silicon oxide coat, in which an average particle diameter of the zinc oxide particles is in a range of more than 50 nm and 500 nm or less, and, when an abundance ratio of silicon in the silicon oxide coat in a $Q^3$ environment is indicated by $Q^3$, and an abundance ratio in a $Q^4$ environment is indicated by $Q^4$, $Q^3+Q^4 \geq 0.6$ and $Q^4/(Q^3+Q^4) \geq 0.5$ are satisfied.

The content rate of the zinc oxide particles is preferably in a range of 50% by mass or more and 99% by mass or less.

When the silicon oxide-coated zinc oxide is immersed in an aqueous solution having a hydrogen-ion exponent of 5 so that the content thereof reaches 0.05% by mass, the elution ratio of zinc being eluted into the aqueous solution is preferably 60% by mass or less.

In a method for producing the silicon oxide-coated zinc oxide of the present invention, zinc oxide particles are suspended in a solvent so as to produce a zinc oxide suspension, next, any one or more of alkoxysilanes and oligomers of alkoxysilanes which are decamer oligomers or smaller, a catalyst, and water are added to and reacted with the zinc oxide suspension, and then the obtained reaction product is thermally treated at a temperature in a range of 150° C. or higher and lower than 600° C.

A composition including a silicon oxide-coated zinc oxide of the present invention includes the silicon oxide-coated zinc oxide of the present invention and a solvent.

A cosmetic of the present invention includes either or both the silicon oxide-coated zinc oxide of the present invention and the composition including a silicon oxide-coated zinc oxide of the present invention in a base.

In addition, as a result of repeating intensive studies in order to solve the above-described problems, the present inventors found that, in silicon oxide-coated zinc oxide formed by coating the surfaces of zinc oxide particles having an average particle diameter in a range of more than 50 nm and 500 nm or less with a silicon oxide coat, when $Q^3+Q^4 \geq 0.6$ and $Q^4/(Q^3+Q^4) \geq 0.5$ are satisfied in which the abundance ratio of silicon in the silicon oxide coat in a $Q^3$ environment is indicated by $Q^3$, and the abundance ratio in a $Q^4$ environment is indicated by $Q^4$, and the decomposition ratio of Brilliant Blue generated by the photocatalytic activity of the zinc oxide particles is set to 3% or less, the silicon oxide coat is capable of inhibiting the elution of zinc ions from the zinc oxide particles. In addition, the present inventors found that, when this silicon oxide-coated zinc oxide is applied to cosmetics, the ultraviolet ray-screening function improves, the transparency is also excellent, and furthermore, the problem attributed to the elution of zinc ions is also solved and completed the present invention.

That is, the silicon oxide-coated zinc oxide of the present invention is a silicon oxide-coated zinc oxide formed by coating the surfaces of zinc oxide particles with a silicon oxide coat, in which the average particle diameter of the zinc oxide particles is in a range of more than 50 nm and 500 nm or less, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and the decomposition ratio of Brilliant Blue generated by the photocatalytic activity of the zinc oxide particles is 3% or less.

The content rate of the zinc oxide particles is preferably in a range of 50% by mass or more and 99% by mass or less.

When the silicon oxide-coated zinc oxide is immersed in an aqueous solution having a hydrogen-ion exponent of 5 so that the content thereof reaches 0.05% by mass, the elution ratio of zinc being eluted into the aqueous solution is preferably 20% by mass or less.

In the method for producing the silicon oxide-coated zinc oxide of the present invention, surface-modified zinc oxide particles are suspended in a solvent so as to produce a surface-modified zinc oxide suspension, next, any one or more of alkoxysilanes and oligomers of alkoxysilanes which are decamer oligomers or smaller, a catalyst, and water are added to and reacted with the surface-modified zinc oxide suspension, and then the obtained reaction product is thermally treated at a temperature in a range of 150° C. or higher and lower than 600° C.

A composition including a silicon oxide-coated zinc oxide of the present invention includes the silicon oxide-coated zinc oxide of the present invention and a solvent.

A cosmetic of the present invention is formed by including either or both the silicon oxide-coated zinc oxide of the present invention and the composition including a silicon oxide-coated zinc oxide of the present invention in a base.

Advantageous Effects of Invention

According to the silicon oxide-coated zinc oxide of the present invention, in the silicon oxide-coated zinc oxide formed by coating the surfaces of zinc oxide particles with a silicon oxide coat, the average particle diameter of the zinc oxide particles is set to more than 50 nm and 500 nm or less, and, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and thus it is possible to prevent zinc ions from being eluted from the zinc oxide particles to the outside by coating the surfaces of the zinc oxide particles with a silicon oxide coat. Therefore, it is possible to prevent zinc ions from being eluted from the silicon oxide-coated zinc oxide particles to the outside. Therefore, it is possible to suppress the degradation of performance of silicon oxide-coated zinc oxides, discoloration, a change in viscosity, and the like due to the elution of zinc ions.

According to the method for producing a silicon oxide-coated zinc oxide of the present invention, since zinc oxide particles are suspended in a solvent so as to produce a zinc oxide suspension, next, any one or more of alkoxysilanes and oligomers of alkoxysilanes which are decamer oligomers or smaller, a catalyst, and water are added to and reacted with the zinc oxide suspension, and then the obtained reaction product is thermally treated at a temperature in a range of 150° C. or higher and lower than 600° C., it is possible to easily and inexpensively produce a silicon oxide-coated zinc oxide capable of preventing zinc ions from being eluted from the zinc oxide particles to the outside.

According to the composition including a silicon oxide-coated zinc oxide of the present invention, since the silicon oxide-coated zinc oxide of the present invention and a solvent are included, it is possible to suppress the elution of zinc ions from the zinc oxide particles in the silicon oxide-coated zinc oxide into the solvent. Therefore, it is possible to suppress the degradation of performance as compositions including a silicon oxide-coated zinc oxide, discoloration, a change in viscosity, and the like due to the elution of zinc ions.

According to the cosmetic of the present invention, since the cosmetic includes either or both the silicon oxide-coated zinc oxide of the present invention and the composition including a silicon oxide-coated zinc oxide of the present invention in a base, it is possible to suppress the elution of a zinc element included in either or both the silicon oxide-coated zinc oxide and the composition including a silicon oxide-coated zinc oxide in a zinc ion form into the base.

Therefore, it is possible to suppress the degradation of performance as cosmetics, discoloration, a change in the viscosity, and the like which are caused by the elution of zinc ions.

In addition, according to the silicon oxide-coated zinc oxide of the present invention, since the surfaces of zinc oxide particles are coated with a silicon oxide coat, the average particle diameter of the zinc oxide particles is set in a range of more than 50 nm and 500 nm or less, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and, furthermore, the decomposition ratio of Brilliant Blue generated by the photocatalytic activity of the zinc oxide particles is set to 3% or less, the surfaces of the zinc oxide particles are uniformly coated with a dense silicon oxide coat, and thus it is possible to suppress the elution of zinc ions from the zinc oxide particles to the outside. Therefore, in a case in which the silicon oxide-coated zinc oxide is applied to a cosmetic, it is possible to suppress the degradation of performance as cosmetics, discoloration, a change in the viscosity, and the like which are caused by the elution of zinc ions.

According to the method for producing the silicon oxide-coated zinc oxide of the present invention, since surface-modified zinc oxide particles are suspended in a solvent so as to produce a surface-modified zinc oxide suspension, next, any one or more of alkoxysilanes and oligomers of alkoxysilanes which are decamer oligomers or smaller, a catalyst, and water are added to and reacted with the surface-modified zinc oxide suspension, and then the obtained reaction product is thermally treated at a temperature in a range of 150° C. or higher and lower than 600° C., it is possible to uniformly cover the surfaces of the zinc oxide particles with a dense silicon oxide coat. Therefore, it is possible to produce a silicon oxide-coated zinc oxide capable of suppressing the elution of zinc ions from the zinc oxide particles.

According to the composition including a silicon oxide-coated zinc oxide of the present invention, since the composition includes the silicon oxide-coated zinc oxide of the present invention and a solvent, it is possible to suppress the elution of a zinc element included in the silicon oxide-coated zinc oxide in a zinc ion form to the outside. Therefore, it is possible to suppress the degradation of performance as compositions, discoloration, a change in the viscosity, and the like which are caused by the elution of zinc ions.

According to the cosmetic of the present invention, since either or both the silicon oxide-coated zinc oxide of the present invention and the composition including a silicon oxide-coated zinc oxide of the present invention are included in a base, it is possible to suppress the elution of a zinc element included in either or both the silicon oxide-coated zinc oxide of the present invention and the composition including a silicon oxide-coated zinc oxide of the present invention in a zinc ion form into the base. Therefore, it is possible to suppress the degradation of performance as cosmetics, discoloration, a change in the viscosity, and the like which are caused by the elution of zinc ions.

DETAILED DESCRIPTION OF THE EMBODIMENTS FOR CARRYING OUT THE INVENTION

First embodiment of the present invention

Figure 1:
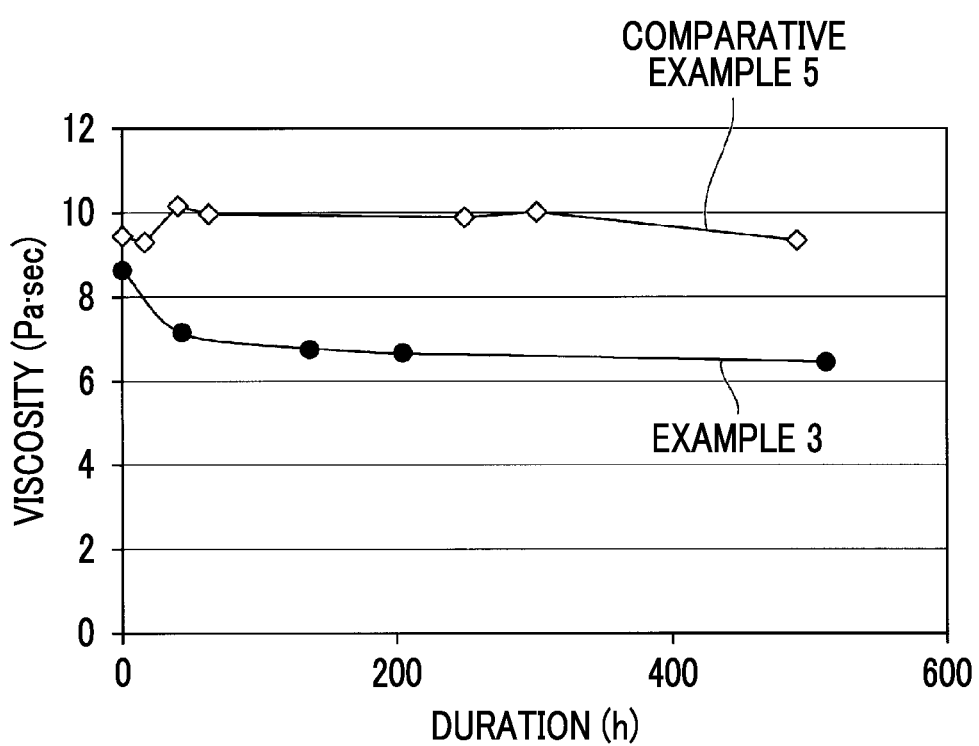
FIG. 1 is a view illustrating changes in viscosity over time at 40° C. of a composition including a silicon oxide-coated zinc oxide of Examples 3 and an aqueous solution of a carbomer of Comparative Example 5 of the present invention.

A first embodiment for carrying out a silicon oxide-coated zinc oxide and a method for producing the same, a composition and a cosmetic including a silicon oxide-coated zinc oxide of the present invention will be described.

Meanwhile, the following embodiments are the specific descriptions for the better understanding of the gist of the present invention and do not limit the present invention unless particularly otherwise described.

[Silicon oxide-coated zinc oxide]

A silicon oxide-coated zinc oxide of a first embodiment of the present invention is a silicon oxide-coated zinc oxide formed by coating the surfaces of zinc oxide particles with a silicon oxide coat, in which the average particle diameter of the zinc oxide particles is in a range of more than 50 nm and 500 nm or less, and, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied.

The content rate of the zinc oxide particles in the silicon oxide-coated zinc oxide is preferably in a range of 50% by mass or more and 99% by mass or less. Here, when the content rate of the zinc oxide particles is lower than 50% by mass, it is impossible to obtain a desired ultraviolet ray-screening effect, and thus it is necessary to use a large amount of silicon oxide-coated zinc oxide in order to obtain a desired ultraviolet ray-screening effect, which is not preferable. On the other hand, when the content rate of the zinc oxide particles exceeds 99% by mass, the fraction of the zinc oxide particles in the silicon oxide-coated zinc oxide becomes too high, and consequently, it becomes impossible to sufficiently cover the surfaces of the zinc oxide particles with a silicon oxide coat, which is not preferable.

The average particle diameter of the silicon oxide-coated zinc oxide is preferably in a range of more than 50 nm and 2,000 nm or less, more preferably in a range of 100 nm or more and 500 nm or less, and still more preferably in a range of 200 nm or more and 300 nm or less.

Here, the reasons for limiting the average particle diameter of the silicon oxide-coated zinc oxide to the above-described range are as described below. When the average particle diameter is 50 nm or less, the particle size of the included zinc oxide also becomes small, and there is a concern that scattering in the ultraviolet range may become relatively small on the long wavelength side. On the other hand, when the average particle diameter exceeds 2,000 nm, in a case in which the silicon oxide-coated zinc oxide is used for a cosmetic or the like, there is a concern that friction or the like may be caused and thus the feeling during the use of the cosmetic or the like may deteriorate.

The "average particle diameter" mentioned herein refers to a numerical value obtained by, when the silicon oxide-coated zinc oxide is observed using a transmission electron microscope (TEM), a scanning electron microscope (SEM), or the like, selecting a predetermined number of the silicon oxide-coated zinc oxide particles, for example, 200 or 100 silicon oxide-coated zinc oxide particles, measuring the longest straight line portions (maximum length diameters) of the respective silicon oxide-coated zinc oxide particles, and obtaining the weighted average value of the measurement values.

Here, in a case in which the silicon oxide-coated zinc oxide particles agglomerate together, instead of measuring the agglomerated particle diameters of the agglomerates, the particle diameters of a predetermined number of particles (primary particles) of the silicon oxide-coated zinc oxide constituting the agglomerate are measured, and the average particle diameter is obtained.

When the silicon oxide-coated zinc oxide is immersed in an aqueous solution having a hydrogen-ion exponent (pH) of 5 for one hour so that the content thereof reaches 0.05% by mass, the elution ratio of zinc being eluted into this aqueous solution is preferably 60% by mass or less, more preferably 50% by mass or less, and still more preferably 30% by mass or less.

The reason for setting the elution ratio of zinc to 60% by mass or less is that, when the elution ratio of zinc exceeds 60 mass%, the stability of the silicon oxide-coated zinc oxide degrades, in a case in which the silicon oxide-coated zinc oxide is applied to a cosmetic, zinc ions being eluted react with a water-soluble macromolecule or the like such as an organic ultraviolet ray-screening agent or a viscosity improver, and the degradation of performance as cosmetics, discoloration, a change in the viscosity, and the like are caused, which is not preferable.

The elution ratio of zinc can be measured by, for example, dispersing the silicon oxide-coated zinc oxide in a buffer solution with a pH of 5 so that the content thereof reaches 0.05% by mass, stirring the solution for one hour, then, separating solids and liquids, and measuring the concentration of liquid-phase zinc using an ICP optical emission spectrometry analyzer.

As the buffer solution with a pH of 5, for example, a buffer solution obtained by mixing 500 ml of an aqueous solution of potassium hydrogen phthalate having a concentration of 0.1 mol and 226 ml of an aqueous solution of sodium hydroxide having a concentration of 0.1 mol and then adding water thereto so that the total amount reaches 1,000 ml is preferably used as long as the buffer solution is capable of dispersing the silicon oxide-coated zinc oxide.

This silicon oxide-coated zinc oxide may be formed by carrying out a surface treatment on the surface thereof using a silicone resin.

When the silicon oxide-coated zinc oxide is surface-treated with a silicone resin, the affinity of the silicon oxide-coated zinc oxide to an oil phase, particularly, a silicone oil, becomes high, and thus it becomes easy to blend the silicon oxide-coated zinc oxide into a water-in-oil (W/O) type or oil-in-water (O/W) type cosmetic.

That is, when the silicon oxide-coated zinc oxide formed by being surface-treated with the silicone resin is blended into an oil phase so as to produce a water-in-oil type or oil-in-water type cosmetic, it is possible to suppress the elution of zinc ions in the water-in-oil (W/O) type or oil-in-water (O/W) type cosmetic.

The silicone resin used in the surface treatment needs to be a resin that can be used as cosmetics and is not particularly limited. Examples thereof include methyl hydrogen polysiloxane, dimethyl polysiloxane, methicone, hydrogen dimethicone, triethoxysilylethyl polydimethylsiloxyethyl dimethicone, triethoxysilylethyl polydimethylsiloxyethyl hexyl dimethicone, (acrylates/tridecyl acrylate/triethoxysilylpropyl methacrylate/dimethicone methacrylate) copolymers, triethoxycaprylylsilane, and the like. These silicone resins may be used singly, a mixture of two or more silicone resins may be used, or a copolymer of these silicone resins may be used.

In a case in which the surface of the silicon oxide-coated zinc oxide is further surface-treated with the silicone resin, the amount of the surface treatment of the silicone resin in the surface treatment may be appropriately adjusted depending on an oil phase being used in water-in-oil type or oil-in-water type cosmetics, and, for example, the amount of the surface treatment thereof is preferably in a range of 1% by mass or more and 20% by mass or less and more preferably in a range of 3% by mass or more and 10% by mass or less in relation to the total mass of the silicon oxide-coated zinc oxide.

Hereinafter, individual constitutional elements of the silicon oxide-coated zinc oxide of the present embodiment will be described in detail.

"Zinc oxide particles"

The average particle diameter of the zinc oxide particles is in a range of more than 50 nm and 500 nm or less, preferably in a range of 100 nm or more and 400 nm or less, and more preferably in a range of 200 nm or more and 300 nm or less.

Here, the reasons for limiting the average particle diameter of the zinc oxide particles to the above-described range will be described below.

Scattering by zinc oxide becomes Rayleigh scattering in a case in which the particle diameter of the zinc oxide is sufficiently smaller than wavelengths, that is, $\alpha \ll 1$ and, generally, $\alpha < 0.4$ in Expression (1) below and becomes Mie-scattering in a case in which the particle diameter is larger than wavelengths. Therefore, in order to obtain the effect of Mie-scattering in the ultraviolet range, particularly, the UV-A range (320 nm or more and 400 nm or less) in which wavelengths are longer, a particle diameter of more than 50 nm is preferred.

$$\alpha = \pi \cdot D/\lambda \quad (1)$$

(Here, $\alpha$ represents the particle diameter parameter, D represents the particle diameter, and $\lambda$ represents the wavelength)

Therefore, in a case in which the average particle diameter of zinc oxide is 50 nm or less, scattering by zinc oxide becomes Rayleigh scattering in which the scattering efficiency is poorer than in Mie-scattering as described above, and there is a concern that a sufficient scattering effect may not be obtained.

On the other hand, in a case in which the average particle diameter of zinc oxide is more than 500 nm, the average particle diameter of the silicon oxide-coated zinc oxide also increases, and there is a concern that transparency in the visible light range or the feeling during use may be impaired in a case in which the silicon oxide-coated zinc oxide is used for cosmetics or the like.

The average particle diameter of the zinc oxide particles can be obtained using the same method for the above-described silicon oxide-coated zinc oxide, that is, a method in which, in a case in which the zinc oxide particles are observed using a transmission electron microscope (TEM) or the like, a predetermined number of the zinc oxide particles, for example, 200 or 100 zinc oxide particles are selected from a microscopic view, the longest straight line portions (maximum length diameters) of the respective zinc oxide particles are measured, and the measurement values are weight-averaged.

As the method for synthesizing the zinc oxide particles, there is no particular limitation as long as zinc oxide particles having an average particle diameter in a range of more than 50 nm and 500 nm or less can be synthesized in the method, and examples thereof include dry methods such as a French method (indirect method) and an American method (direct method) and wet methods such as a German method.

"Silicon oxide coat"

The silicon oxide coat is not particularly limited as long as the silicon oxide coat has a high degree of condensation so that "when the abundance ratio of silicon in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$", which will be described below, are satisfied.

The degree of condensation of silicon oxide can be easily determined by measuring the NMR spectrum of the silicon oxide-coated zinc oxide using solid-state $^{29}$Si MAS-nuclear magnetic resonance (NMR) spectroscopy and measuring the area ratios of signals attributed to individual environments of $Q^0$, $Q^1$, $Q^2$, $Q^3$, and $Q^4$ from the peak area ratios of the NMR spectrum.

Here, $Q^n$ (n=0 or more and 4 or less) indicates a chemical structure determined depending on the number of bridging oxygen atoms, that is, oxygen atoms that are bonded to two Si atoms, out of oxygen atoms in a $SiO_4$ tetrahedral unit which is a constituent unit of silicon oxide.

The area ratios of the signals attributed to these respective environments of $Q^0$, $Q^1$, $Q^2$, $Q^3$, and $Q^4$ are marked as $Q^0$, $Q^1$, $Q^2$, $Q^3$, and $Q^4$. Here, $Q^0+Q^1+Q^2+Q^3+Q^4=1$.

When the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied.

Here, in a case in which $Q^3+Q^4 \geq 0.6$ is satisfied, but $Q^4/(Q^3+Q^4)$ is smaller than 0.5 ($Q^4/(Q^3+Q^4)<0.5$) or in a case in which $Q^4/(Q^3+Q^4) \geq 0.5$ is satisfied, but $Q^3+Q^4$ is smaller than 0.6 ($Q^3+Q^4<0.6$), silicon oxide in the silicon oxide coat does not sufficiently condense, and thus a dense coat cannot be obtained, and consequently, there is a concern that the effect of suppressing the elution of zinc ions in the silicon oxide-coated zinc oxide may not be sufficiently obtained, which is not preferable.

[Method for producing silicon oxide-coated zinc oxide]

A method for producing the silicon oxide-coated zinc oxide of the present embodiment is a method including a zinc oxide suspension production step of producing a zinc oxide suspension by suspending zinc oxide particles in a solvent, a reaction step of adding any one or more of alkoxysilanes and oligomers of alkoxysilanes which are decamer oligomers or smaller, a catalyst, and water to the zinc oxide suspension and causing a reaction, and a thermal treatment step of thermally treating the obtained reaction product at a temperature in a range of 150° C. or higher and lower than 600° C.

"Zinc oxide suspension production step"

This is a step of producing a zinc oxide suspension by suspending zinc oxide particles in a solvent.

Here, the average particle diameter of the zinc oxide particles that are used herein is more than 50 nm and 500 nm or less, preferably 100 nm or more and 400 nm or less, and more preferably 200 nm or more and 300 nm or less.

Here, the solvent that suspends zinc oxide particles is not particularly limited as long as the solvent is capable of suspending zinc oxide particles, and, in addition to water, alcohols such as methanol, ethanol, 1-propanol, 2-propanol, 1-butanol, 2-butanol, and octanol, esters such as ethyl acetate, butyl acetate, ethyl lactate, propylene glycol monomethyl ether acetate, propylene glycol monoethyl ether acetate, and γ-butyrolactone, and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether can be preferably used.

In addition, ketones such as acetone, methyl ethyl ketone, methyl isobutyl ketone, acetyl acetone, and cyclohexanone, aromatic hydrocarbons such as benzene, toluene, xylene, and ethyl benzene, and amides such as dimethylformamide, N,N-dimethylacetoacetamide, and N-methyl pyrrolidone can be preferably used.

These solvents may be used singly, or a mixture of two or more solvents may be used.

The content rate of the zinc oxide particles in the zinc oxide suspension is preferably in a range of 1% by mass or more and 80% by mass or less, more preferably in a range of 20% by mass or more and 70% by mass or less, and still more preferably in a range of 30% by mass or more and 60% by mass or less.

The reasons for setting the content rate of the zinc oxide particles in the zinc oxide suspension in a range of 1% by mass or more and 80% by mass or less are as described below. When the content rate of the zinc oxide particles is less than 1% by mass, it is necessary to remove a large amount of the solvent compared with the content of the zinc oxide particles in the suspension, and there is a concern of an increase in cost. On the other hand, when the content rate exceeds 80% by mass, the viscous property of the suspension increases (the suspension becomes more viscous), and thus the dispersion stability of the zinc oxide particles degrades, and there is a concern that the zinc oxide particles may easily settle out.

Regarding the method for suspending the zinc oxide particles in the solvent, there is no particular limitation, and a well-known suspension method can be used. For example, a beads mill in which media such as zirconia beads are used, a ball mill, a homogenizer, a disper, a stirrer, or the like can be preferably used. The time necessary for a suspension treatment needs to be a sufficient time for the zinc oxide particles to be uniformly suspended in the solvent.

In this case, a dispersant may be added as necessary.

"Reaction step"

This is a step of adding any one or more of alkoxysilanes and oligomers of alkoxysilanes which are decamer oligomers or smaller, a catalyst, and water to the zinc oxide suspension and stirring the components for approximately 30 minutes or longer and 24 hours or shorter, thereby causing a reaction.

Here, the reason for limiting the component to be added to alkoxysilanes and oligomers of alkoxysilanes which are decamer oligomers or smaller is to obtain a dense silicon oxide coat having a high degree of condensation of silicon oxide.

Meanwhile, in a case in which a silicate of alkaline metal is used instead of the alkoxysilane, it is difficult to improve the degree of condensation of silicon oxide in the silicon oxide coat, and a dense silicon oxide coat cannot be obtained, which is not preferable.

In addition, the reasons for limiting the oligomers of alkoxysilanes to decamer oligomers or smaller of alkoxysilanes are that, when the chain length of the oligomer becomes long, the distance between the oligomers becomes easily opened, and, in the case of an undecamer oligomer or larger, even when a thermal treatment is carried out after the zinc oxide particles are coated, silicon oxide in the coat does not sufficiently condense, and thus a dense silicon oxide coat cannot be obtained, and there is a concern that a desired elution-suppressing effect may not be obtained.

The alkoxysilane is preferably a tetraalkoxysilane, and the oligomer of an alkoxysilane which is a decamer oligomer or smaller is preferably an oligomer of a tetraalkoxysilane which is a decamer oligomer or smaller.

The tetraalkoxysilane is expressed by General Formula (2) described below:

$$Si(OR)_4 \qquad (2)$$

(Here, R represents an alkoxyl group (RO group), and these four alkoxyl groups (RO groups) may be all identical to each other or may be partially or all different from each other). The number of carbon atoms in the alkoxyl group is preferably in a range of 1 or more and 8 or less.

Examples of the tetraalkoxysilane include tetramethoxysilane, tetraethoxysilane, tetra-n-propoxysilane, tetraisopropoxysilane, tetra-n-butoxysilane, tetraisobutoxysilane, tetra-sec-butoxysilane, tetra-t-butoxysilane, tetraphenoxysilane, monoethoxytrimethoxysilane, monobutoxytrimethoxysilane, monopentoxytrimethoxysilane, monohexoxytrimethoxysilane, dimethoxydiethoxysilane, dimethoxydibutoxysilane, and the like.

Among these, tetramethoxysilane and tetraethoxysilane can be preferably used since tetramethoxysilane and tetraethoxysilane have a high content of Si, the concentration thereof can be easily controlled when tetramethoxysilane and tetraethoxysilane are dispersed in the solvent, and tetramethoxysilane and tetraethoxysilane have a high hydrolysis and condensation reactivity.

These tetraalkoxysilanes may be used singly or a mixture of two or more tetraalkoxysilanes may be used.

In addition, an oligomer of the tetraalkoxysilane which is a decamer oligomer or smaller can be obtained by adding water to monomers of one or more tetraalkoxysilanes and hydrolyzing and condensing the monomers to a certain extent.

Examples of commercially available products of the oligomer of the tetraalkoxysilane include MKC SILICATE MS51 (manufactured by Mitsubishi Chemical Corporation), METHYL SILICATE 51 (tetramer on average), METHYL SILICATE 53A (heptamer on average), ETHYL SILICATE 40 (pentamer on average), ETHYL SILICATE 48 (decamer on average) (all manufactured by Colcoat Co., Ltd.), and the like.

One or more of the tetraalkoxysilane and the oligomers of the tetraalkoxysilane which are decamer oligomers or smaller are preferably added thereto so that the content thereof falls in a range of 2% by mass or more and 45% by mass or less in relation to the zinc oxide particles in the zinc oxide suspension when converted to silicon oxide.

The catalyst is added thereto for the purpose of accelerating the hydrolysis or condensation polymerization reaction of the tetraalkoxysilane and the oligomers of the tetraalkoxysilane which are decamer oligomers or smaller. As the catalyst, a well-known acidic catalyst or basic catalyst can be used (refer to Sumio Sakka's "Science of Sol-Gel Process" published by Agne Shofu Co., Ltd., Chapter 9 (p. 154 top. 173)).

Examples of the acidic catalyst include inorganic acids such as hydrochloric acid, sulfuric acid, nitric acid, and phosphoric acid; and organic acids such as formic acid, acetic acid, oxalic acid, lactic acid, and tartaric acid, and among these, an inorganic acid, in particular, hydrochloric acid can be preferably used. In addition, the acidic catalysts may be used singly or a combination of two or more acidic catalysts may be used.

Examples of basic catalysts include sodium hydroxide, potassium hydroxide, lithium hydroxide, cerium hydroxide, barium hydroxide, calcium hydroxide, pyridine, pyrrole, piperazine, pyrrolidine, piperidine, picoline, ammonia, methylamine, ethylamine, propylamine, butylamine, dimethylamine, diethylamine, dipropylamine, dibutylamine, trimethylamine, triethylamine, tripropylamine, tributylamine, monoethanolamine, diethanolamine, dimethylmonoethanolamine, monomethyldiethanolamine, triethanolamine, diazabicyclooctane, diazabicyclononane, diazabicycloundecene, urea, tetramethylammonium hydroxide, tetraethylammonium hydroxide, tetrapropylammonium hydroxide, tetrabutylammonium hydroxide, benzyltrimethylammonium hydroxide, choline, and the like.

Among these, ammonia, organic amines, and ammonium hydroxides can be preferably used. These basic catalysts may be used singly or a combination of two or more basic catalysts may be used.

As the catalyst, either the acidic catalyst or the basic catalyst may be used, but the acidic catalyst, which is an electrophilic reaction agent, can be preferably used.

The reaction temperature is not particularly limited as long as the hydrolysis or condensation polymerization reaction of the tetraalkoxysilane and the oligomers of the tetraalkoxysilane which are decamer oligomers or smaller rapidly proceeds at the reaction temperature, but the reaction temperature is preferably in a range of 0° C. or higher and 100° C. or lower, more preferably in a range of 20° C. or higher and 80° C. or lower, and still more preferably in a range of 40° C. or higher and 60° C. or lower.

The amount of water added needs to be large enough to hydrolyze one or more of the tetraalkoxysilane and the oligomers of the tetraalkoxysilane which are decamer oligomers or smaller, that is, to make the hydrolysis ratio reach 100% or greater.

As a result, the hydrolysis reaction of one or more of the alkoxysilane and the oligomers of the alkoxysilane which are decamer oligomers or smaller proceeds, and a condensation reaction also proceeds, thereby obtaining a reaction liquid.

The reaction liquid is separated into solids and liquids through normal-pressure filtration, reduced-pressure filtration, pressurization filtration, centrifugal separation, or the like, thereby obtaining a solid-phase reaction product.

"Thermal treatment step"

This is a step of thermally treating the above-described reaction product at a temperature in a range of 150° C. or higher and lower than 600° C.

The thermal treatment of the reaction product is preferably in a range of 250° C. or higher and 550° C. or lower and more preferably in a range of 300° C. or higher and 500° C. or lower in order to accelerate the densification of the silicon oxide coat.

The reasons for limiting the thermal treatment temperature in a range of 150° C. or higher and lower than 600° C. are as described below. When the thermal treatment temperature is lower than 150° C., a dense silicon oxide coat that has been sufficiently condensed cannot be obtained, and consequently, there is a concern that an effect of suppressing the elution of zinc ions from the zinc oxide particles may not be sufficiently obtained. On the other hand, when thermal treatment temperature is 600° C. or higher, the silicon oxide-coated zinc oxides having the silicon oxide coat formed thereon are bonded to each other, thus, coarse particles are formed or zinc oxide grains grow, and consequently, in a case in which a cosmetic into which the silicon oxide-coated zinc oxide is blended is used, there is a concern that sufficient transparency may not be obtained in the visible light range.

As long as the thermal treatment temperature is in a range of 150° C. or higher and lower than 600° C., the thermal treatment step may be repeated multiple times at a predetermined temperature in the above-described temperature range or may be repeated multiple times at different temperatures in the above-described range.

In a case in which the surfaces of the silicon oxide-coated zinc oxide obtained in the above-described manner are further surface-treated with the silicone resin, it is possible to use a well-known method such as a method in which the silicon oxide-coated zinc oxide that has been subjected to the thermal treatment step and the silicone resin are directly mixed together (dry treatment method) or a method in which the silicon oxide-coated zinc oxide that has been subjected to the thermal treatment step is dispersed in a solution including the silicone resin, then, the solvent in the solution is removed, and then a heating treatment is carried out (wet treatment method).

In a case in which the silicon oxide-coated zinc oxide that has been subjected to the thermal treatment step is dispersed in a solution including the silicone resin, the silicon oxide-coated zinc oxide is preferably mixed with the solution so that the content rate of the silicon oxide-coated zinc oxide falls in a range of 10% by mass or more and 40% by mass or less and preferably falls in a range of 25% by mass or more and 35% by mass or less in the solution including the silicone resin. When the silicon oxide-coated zinc oxide is mixed in the above-described range, it is possible to improve the production efficiency.

In a case in which the surface treatment is carried out using the silicone resin, the heating treatment is preferably carried out in a temperature range of 100° C. or higher and 300° C. or lower. When the heating treatment is carried out in the above-described temperature range, it is possible to surface-treat the surfaces of the silicon oxide-coated zinc oxide with the silicone resin and suppress the thermal decomposition of the silicone resin and the crystal growth of zinc oxide.

Through the above-described steps, the silicon oxide-coated zinc oxide of the present embodiment can be produced.

[Composition including silicon oxide-coated zinc oxide]

A composition including a silicon oxide-coated zinc oxide of the present embodiment includes the above-described silicon oxide-coated zinc oxide and a solvent.

The average particle diameter of the silicon oxide-coated zinc oxide is preferably in a range of more than 50 nm. and 2,000 nm or less, more preferably in a range of 100 nm or more and 500 nm or less, and still more preferably in a range of 200 nm or more and 300 nm or less.

Here, the reasons for limiting the average particle diameter of the silicon oxide-coated zinc oxide to the above-described range are as described below. When the average particle diameter thereof is 50 nm or less, the particle size of the included zinc oxide also becomes small, and there is a concern that scattering in the ultraviolet range may become relatively small on the long wavelength side, and, when the average particle diameter exceeds 2,000 nm, in a case in which the silicon oxide-coated zinc oxide is used for a cosmetic or the like, there is a concern that friction or the like may be caused and thus the feeling during the use of the cosmetic or the like may deteriorate.

The average dispersed-particle diameter of the silicon oxide-coated zinc oxide in the composition including a silicon oxide-coated zinc oxide is preferably in a range of 60 nm or more and 10 µm or less, more preferably in a range of 80 nm or more and 7 µm or less, and still more preferably in a range of 100 nm or more and 5 µm or less.

Here, the reasons for limiting the average dispersed-particle diameter of the silicon oxide-coated zinc oxide to the above-described range are as described below. When the average dispersed-particle diameter is less than 60 nm, there is a concern that scattering in the ultraviolet range may become relatively small on the long wavelength side, which is not preferable. On the other hand, when the average dispersed-particle diameter exceeds 10 µm, there is a concern that transparency may degrade when the composition including a silicon oxide-coated zinc oxide is blended into cosmetics, which is not preferable.

The content rate of the silicon oxide-coated zinc oxide in the composition including a silicon oxide-coated zinc oxide may be appropriately adjusted in order to obtain desired ultraviolet ray-screening function, and is not particularly limited, but the content rate thereof is preferably in a range of 1% by mass or more and 80% by mass or less, more preferably in a range of 20% by mass or more and 70% by mass or less, and still more preferably in a range of 30% by mass or more and 60% by mass or less.

The reasons for limiting the content rate of the silicon oxide-coated zinc oxide to a range of 1% by mass or more and 80% by mass or less are as described below. When the content rate of the silicon oxide-coated zinc oxide is less than 1% by mass, there is a concern that the composition may become incapable of exhibiting a sufficient ultraviolet ray-screening function, thus, when this composition is blended into a cosmetic or the like, it is necessary to add a large amount of the composition in order to exhibit a desired ultraviolet ray-screening function, and there is a concern that the manufacturing cost may become high, which is not preferable. On the other hand, when the content rate exceeds 80% by mass, the viscous property of the composition increases, and thus the dispersion stability of the silicon oxide-coated zinc oxide degrades, and there is a concern that the silicon oxide-coated zinc oxide may easily settle out, which is not preferable.

Here, the solvent is not particularly limited as long as the solvent is capable of dispersing the silicon oxide-coated zinc oxide, and, for example, water, alcohols such as methanol, ethanol, 1-propanol, 2-propanol, 1-butanol, 2-butanol, octanol, and glycerin, esters such as ethyl acetate, butyl acetate, ethyl lactate, propylene glycol monomethyl ether acetate, propylene glycol monoethyl ether acetate, and y-butyrolactone; and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether can be preferably used.

In addition, ketones such as acetone, methyl ethyl ketone, methyl isobutyl ketone, acetyl acetone, and cyclohexanone; aromatic hydrocarbons such as benzene, toluene, xylene, and ethyl benzene; cyclic hydrocarbons such as cyclohexane; amides such as dimethylformamide, N,N-dimethylacetoacetamide, and N-methyl pyrrolidone; and chain-like polysiloxanes such as dimethylpolysiloxane, methyl phenyl polysiloxane, and diphenyl polysiloxane can also be preferably used.

In addition, cyclic polysiloxanes such as octamethylcyclotetrasiloxane, decamethylcyclopentasiloxane, and dodecamethylcyclohexasiloxane; and modified polysiloxanes such as amino-modified polysiloxane, polyether-modified polysiloxane, alkyl-modified polysiloxane, and fluorine-modified polysiloxane can also be preferably used.

These may be used singly, or a mixture of two or more solvents may be used.

The composition including a silicon oxide-coated zinc oxide of the present embodiment may include ordinarily-used additives such as a dispersant, a stabilizer, a water-soluble binder, and a viscosity improver as long as the characteristics thereof are not impaired.

As the dispersant, an anionic surfactant, a cationic surfactant, an ampholytic surfactant, a non-ionic surfactant, a silane coupling agent such as an organoalkoxysilane or organochlorosilane, or a modified silicone such as a polyether-modified silicone or an amino-modified silicone is preferably used. The kind and amount of the dispersant may be appropriately selected depending on the particle diameter of the silicon oxide-coated zinc oxide and the kind of the target dispersion medium, and the dispersant may be used singly or a mixture of two or more dispersants may be used.

As the water-soluble binder, a polyvinyl alcohol (PVA), polyvinyl pyrrolidone, hydroxycellulose, polyacrylic acid, or the like can be used.

Regarding the viscosity improver, in a case in which the composition including a silicon oxide-coated zinc oxide is applied to a cosmetic, there is no particular limitation as long as the viscosity improver can be used for cosmetics. Examples of the viscosity improver that can be preferably used include natural water-soluble macromolecules such as gelatin, casein, collagen, hyaluronic acid, albumin, and starch, semisynthetic macromolecules such as methyl cellulose, ethyl cellulose, methylhydroxypropyl cellulose, carboxymethyl cellulose, hydroxymethyl cellulose, hydroxypropyl cellulose, sodium carboxymethyl cellulose, and alginic acid propylene glycol ester, synthetic macromolecules such as polyvinyl alcohol, polyvinyl pyrrolidone, carbomers (carboxyvinyl polymer), polyacrylate, and polyethylene oxide, inorganic minerals such as bentonite, laponite, and hectorite. The viscosity improvers may be used singly or a combination of two or more viscosity improvers may be used.

Among these viscosity improvers, the synthetic macromolecule is preferred, and a carbomer is more preferred.

Here, in a case in which a carbomer is used as the viscosity improver, the content rate of the carbomer in the composition including a silicon oxide-coated zinc oxide is preferably in a range of 0.01% by mass or more and 10% by mass or less and more preferably in a range of 0.01% by mass or more and 3% by mass or less.

When the content rate of the carbomer in the composition including a silicon oxide-coated zinc oxide is lower than 0.01% by mass, there is a concern that it may become impossible to obtain a viscosity-improving effect, and, on the other hand, when the content rate of the carbomer exceeds 10% by mass, the viscosity becomes too high, and there are disadvantages that, in a case in which the composition including a silicon oxide-coated zinc oxide is applied to cosmetics, the spreading of cosmetics on the skin may become bad when the cosmetics are applied and spread onto the skin and the feeling during the use of the cosmetics may deteriorate, which is not preferable from the viewpoint of use.

In addition, in a case in which a carbomer is used as the viscosity improver, the hydrogen-ion exponent (pH) of the composition including a silicon oxide-coated zinc oxide is preferably in a range of 5 or more and 10 or less, more preferably in a range of 6 or more and 10 or less, and still more preferably in a range of 7 or more and 9 or less.

When the pH of the composition including a silicon oxide-coated zinc oxide is set in the above-described range, it is possible to suppress a change in the viscosity and the like over time.

Meanwhile, carbomers (carboxyvinyl polymer) are widely used as a viscosity improver for water-based cosmetics, but the carbomer improves the viscosity (gelatification) using the interaction between carboxyl groups or between carboxylate groups, and thus the presence of zinc ions breaks the network structure of the carbomer and disables the maintenance of a constant viscous property. Therefore, when several percent by mass of zinc oxide is mixed into an aqueous solution of a carbomer having an adjusted viscosity, the viscosity decreases within several hours.

In addition, even in a case in which zinc oxide having a surface activity suppressed by coating the surface with an inorganic oxide or a resin is used, in many cases, the viscosity decreases or phases separate within several hours to several days. Therefore, in a case in which a carbomer and zinc oxide are jointly used, there is a requirement to suppress or reduce a decrease in the viscosity of a mixture including a carbomer and zinc oxide.

In addition, in a case in which a decrease in the viscosity of an aqueous solution of a carbomer is suppressed using zinc oxide having a surface activity suppressed by coating the surface with an inorganic oxide or a resin of the related art, there is a frequent significant problem of a decrease in the viscosity after a certain period of time elapses rather than a decrease in the viscosity in the initial phase.

The decrease in the viscosity in the initial phase can be coped with by, for example, setting the viscosity of the aqueous solution of a carbomer to be high in advance; however, when the viscosity changes in the middle to long term after a certain period of time elapses, the properties of cosmetics change during the distribution of the cosmetics, and the aging stability is impaired. Particularly, zinc oxide having a surface treated with an inorganic oxide or a resin has a certain degree of an elution-suppressing effect, and thus there has been a concern that zinc ions may be gradually eluted in the middle to long term.

In addition, in the related art, there have been only a small number of reported cases regarding the change of the viscosity of a composition including a carbomer, and, even in the reported cases, only an effect of suppressing a change in the viscosity over time at room temperature for approximately seven days has been confirmed.

In the composition including a silicon oxide-coated zinc oxide of the present embodiment, since a silicon oxide-coated zinc oxide having a stronger zinc elution-suppressing effect than zinc oxide coated with an inorganic oxide or a resin of the related art is used, even when a carbomer is used as the viscosity improver, the viscosity decreases only slightly over time, and thus it is possible to obtain a composition having excellent product stability for a long period of time.

In the composition including a silicon oxide-coated zinc oxide of the present embodiment, the value obtained by dividing the viscosity under acceleration conditions under which chemical reactions are accelerated, for example, the viscosity of the composition after 300 hours of being stored at 40° C., by the viscosity that decreases in the initial phase, for example, the viscosity after 15 hours is preferably in a range of 0.8 or more and 1.2 or less.

As described above, when the value obtained by dividing the viscosity after 300 hours under acceleration conditions by the viscosity that decreases in the initial phase is set in the above-described range, it is possible to maintain the viscosity of the composition including a silicon oxide-coated zinc oxide in the middle to long term, and the aging stability becomes excellent.

In the composition including a silicon oxide-coated zinc oxide of the present embodiment, in a case in which the content rate of the silicon oxide-coated zinc oxide is set to 15% by mass and a 32 μm-thick coat is produced using the composition, the transmission of light having a wavelength of 450 nm is preferably 50% or higher, more preferably 60% or higher, and still more preferably 70% or higher.

The transmission can be obtained by applying the composition including a silicon oxide-coated zinc oxide containing 15% by mass of the silicon oxide-coated zinc oxide onto a silica substrate using a bar coater so as to form a 32 μm-thick coat, and measuring the spectral transmission of the coat using a SPF analyzer UV-1000S (manufactured by Labsphere, Inc.).

The method for producing the composition including a silicon oxide-coated zinc oxide of the present embodiment is not particularly limited as long as the silicon oxide-coated zinc oxide can be dispersed in the above-described solvent.

As the above-described dispersion method, a well-known dispersion method can be used. For example, in addition to a stirrer, a beads mill in which zirconia beads are used, a ball mill, a homogenizer, an ultrasonic disperser, a kneader, a three roll mill, a rotation-revolution mixer, or the like can be preferably used.

The time necessary for a dispersion treatment needs to be a sufficient time for the silicon oxide-coated zinc oxide to be uniformly dispersed in the solvent.

Next, as specific examples of the composition including a silicon oxide-coated zinc oxide of the present embodiment, (1) a silicone resin-based composition including a silicon oxide-coated zinc oxide in which the silicon oxide-coated zinc oxide is dispersed in a silicone resin that is a non-water-soluble dispersion medium and (2) a water-based composition including a silicon oxide-coated zinc oxide in which the silicon oxide-coated zinc oxide is dispersed in water will be respectively described.

"Silicone resin-based composition including silicon oxide-coated zinc oxide"

The silicone resin-based composition including a silicon oxide-coated zinc oxide is a silicone resin-based composition in which the silicon oxide-coated zinc oxide is dispersed in a silicone resin, in which the content rate of the silicon oxide-coated zinc oxide is set in a range of 1% by mass or more and 80% by mass or less, more preferably set in a range of 20% by mass or more and 70% by mass or less, and still more preferably in a range of 30% by mass or more and 60% by mass or less.

The average particle diameter of the silicon oxide-coated zinc oxide is preferably in a range of more than 50 nm. and 2,000 μm or less, more preferably in a range of 100 nm or more and 500 nm or less, and still more preferably in a range of 200 nm or more and 300 nm or less.

The average dispersed-particle diameter of the silicon oxide-coated zinc oxide in the silicone resin-based composition including a silicon oxide-coated zinc oxide is preferably in a range of 60 nm or more and 10 µm or less, more preferably in a range of 80 nm or more and 7 µm or less, and still more preferably in a range of 100 nm or more and 5 µm or less.

The silicone resin is not particularly limited as long as the silicone resin can be used in a cosmetic, and, for example, a cyclic silicone resin, a chain-like silicone resin, or the like can be used.

Examples of the silicone resin include chain-like siloxanes such as dimethyl polysiloxane, methyl phenyl polysiloxane, diphenyl polysiloxane, and methyl hydrogen polysiloxane, cyclic siloxanes such as hexamethylcyclotrisiloxane, octamethylcyclotetrasiloxane, decamethyl pentasiloxane, decamethylcyclopentasiloxane, dodecamethylcyclohexasiloxane, and tetramethyltetrahydrogen polysiloxane, modified silicones such as amino-modified silicone, polyether-modified silicone, and alkyl-modified silicone, methyl trimethicone, and the like.

These silicone resins may be used singly or a mixture of two or more silicone resins may be used.

The silicone resin-based composition including a silicon oxide-coated zinc oxide may include a dispersant.

Examples of the dispersant include modified silicones such as polyether-modified silicone, polyglycerin-modified silicone, amino-modified silicone, phenyl-modified silicone, alkyl-modified silicone, carbinol-modified silicone, and dimethyl silicone; surfactants such as an anionic surfactant, a cationic surfactant, an ampholytic surfactant, and a nonionic surfactant; and silane coupling agents such as an organoalkoxysilane and organochlorosilane.

These dispersants may be used singly or a mixture of two or more dispersants may be used.

The amount of the dispersant added is preferably in a range of 1% by mass or more and 50% by mass or less in relation to the mass of the silicon oxide-coated zinc oxide in the silicone resin-based composition including a silicon oxide-coated zinc oxide.

When the amount of the dispersant added is adjusted to be in the above-described range, even in a case in which the silicone resin-based composition including a silicon oxide-coated zinc oxide is used singly or is directly mixed into a cosmetic, transparency can be sufficiently ensured in a case in which the composition is applied and spread onto the skin.

In addition, into the silicone resin-based composition including a silicon oxide-coated zinc oxide, a natural oil, a moisturizing agent, a viscosity improver, a perfume, a preservative, and the like may be further mixed as long as the characteristics of the composition are not impaired.

The silicone resin-based composition including a silicon oxide-coated zinc oxide may also be made into an oil phase, be emulsified with an aqueous component, and thus be made into an emulsified composition.

The oil phase preferably contains at least one of a higher alcohol and a higher fatty acid and more preferably contains both a higher alcohol and a higher fatty acid. When these components are contained in the oil phase, a firm skin feeling and a moisturized feeling improve, and the sustainability of these effects improves.

The higher alcohol is not particularly limited as long as the higher alcohol can be used as a cosmetic. For example, capryl alcohol, lauryl alcohol, stearyl alcohol, oleyl alcohol, myristyl alcohol, cetyl alcohol, cholesterol, phytosterol, and the like can be preferably used. These may be used singly or a mixture of two or more higher alcohols may be used.

As the higher fatty acid, a saturated or unsaturated fatty acid having 12 to 24 carbon atoms is preferably used, and, for example, myristic acid, palmitic acid, stearic acid, isostearic acid, linoleic acid, arachidonic acid, and the like are preferably used. These may be used singly or a combination of two or more higher fatty acids may be used.

Into this oil phase, an oil-soluble preservative, an ultraviolet absorber, an oil-soluble chemical, an oil-soluble pigment, an oil-soluble protein, a vegetable oil, an animal oil, and the like may be appropriately mixed as necessary.

The method for producing the silicone resin-based composition including a silicon oxide-coated zinc oxide is not particularly limited as long as it is possible to disperse the silicon oxide-coated zinc oxide in the silicone resin.

As the above-described dispersion method, a well-known dispersion device can be used. As the above-described dispersion device, for example, a stirrer, a beads mill, a ball mill, a homogenizer, an ultrasonic disperser, a kneader, a three roll mill, a rotation-revolution mixer, or the like can be preferably used.

The time necessary for a dispersion treatment needs to be a sufficient time for the silicon oxide-coated zinc oxide to be uniformly dispersed in the silicone resin and is not particularly limited.

"Water-based composition including silicon oxide-coated zinc oxide"

The water-based composition including a silicon oxide-coated zinc oxide is a water-based composition formed by dispersing the silicon oxide-coated zinc oxide in a water-based dispersion medium including an alcohol, in which the content rate of the silicon oxide-coated zinc oxide is in a range of 1% by mass or more and 80% by mass or less, more preferably in a range of 20% by mass or more and 70% by mass or less, and still more preferably in a range of 30% by mass or more and 60% by mass or less, and 5% by mass or more and 20% by mass or less of a water-based dispersion medium containing an alcohol is included.

The average particle diameter of the silicon oxide-coated zinc oxide is preferably in a range of more than 50 nm. and 2,000 µm or less, more preferably in a range of 100 nm or more and 500 nm or less, and still more preferably in a range of 200 nm or more and 300 nm or less.

The average dispersed-particle diameter of the silicon oxide-coated zinc oxide in the water-based composition including a silicon oxide-coated zinc oxide is preferably in a range of 60 nm or more and 10 µm or less, more preferably in a range of 80 nm or more and 7 µm or less, and still more preferably in a range of 100 nm or more and 5 µm or less.

Here, the water-based dispersion medium containing an alcohol is a dispersion medium including an alcohol and water, and examples of the alcohol include monovalent or polyvalent alcohols having 1 to 6 carbon atoms such as ethanol, 1-propanol, 2-propanol, 1-butanol, 2-butanol, octanol, glycerin, 1,3-butylene glycol, propylene glycol, and sorbitol. Among these, monovalent alcohols are preferred, and ethanol is particularly preferred.

In a case in which the water-based composition is made up of the silicon oxide-coated zinc oxide and the water-based dispersion medium including the alcohol, the content rate of the alcohol is preferably in a range of 5% by mass or more and 20% by mass or less, and more preferably in a range of 10% by mass or more and 20% by mass or less.

Particularly, in a case in which the content rate of the alcohol is set in a range of 10% by mass or more and 20% by mass or less, it is possible to improve the dispersibility and the aging stability of the silicon oxide-coated zinc oxide in the water-based composition, which is preferable.

The water-based composition including a silicon oxide-coated zinc oxide may further include a water-soluble macromolecule in a range of 0.001% by mass or more and 10% by mass or less, more preferably in a range of 0.005% by mass or more and 5% by mass or less, and still more preferably in a range of 0.01% by mass or more and 3% by mass or less. In this case, it is necessary to adjust the content rates of the respective components so that the total of the respective content rates of the silicon oxide-coated zinc oxide, the water-based dispersion medium including an alcohol, and the water-soluble macromolecule does not exceed 100% by mass.

In a case in which the water-based composition including a silicon oxide-coated zinc oxide is applied to a cosmetic, the water-soluble macromolecule included in the water-based composition is not particularly limited as long as the macromolecule can be used in cosmetic use, and examples thereof include gum arabic, sodium alginate, casein, carrageenan, galactan, carboxyvinyl polymers, carboxymethyl cellulose, sodium carboxymethyl cellulose, carboxymethyl starch, agar, xanthan gum, quince seed, guar gum, collagen, gelatin, cellulose, dextran, dextrin, tragacanth gum, hydroxyethyl cellulose, hydroxypropyl cellulose, sodium hyaluronate pectin, pullulan, methyl cellulose, and methylhydroxypropyl cellulose. These water-soluble macromolecules may be used singly, or a mixture of two or more water-soluble macromolecules may be used.

The water-soluble macromolecule plays roles as a dispersant and a viscosity adjuster, and, when added to the water-based composition, also improves the dispersibility and the aging stability of the silicon oxide-coated zinc oxide in the water-based composition.

In a case in which the water-based composition includes the water-soluble macromolecule, the content rate of the alcohol is preferably in a range of 5% by mass or more and 20% by mass or less and more preferably in a range of 15% by mass or more and 20% by mass or less.

The reasons for setting the content rate of the alcohol in a range of 5% by mass or more and 20% by mass or less in a case in which the water-based composition includes the water-soluble macromolecule are as described below. When the content rate thereof is lower than 5% by mass, the content of the alcohol is too small, and thus the water-soluble macromolecule cannot uniformly infiltrate into the alcohol and unevenly swells due to moisture, and consequently, the dispersibility of the silicon oxide-coated zinc oxide degrades, handling becomes difficult, and furthermore, the aging stability of the water-based composition degrades, which is not preferable.

In addition, when the content rate thereof exceeds 20% by mass, the viscous property of the entire water-based composition becomes high, the dispersion stability of the silicon oxide-coated zinc oxide degrades, and the aging stability of the water-based composition also degrades, which is not preferable.

The water-based composition including a silicon oxide-coated zinc oxide can be obtained by mixing the silicon oxide-coated zinc oxide into the water-based dispersion medium including the alcohol or the water-based dispersion medium including the alcohol and the water-soluble macromolecule, and then mixing water into the mixture so as to disperse the above-described components. The amount of water may be appropriately adjusted and is preferably in a range of 15% by mass or more and 94% by mass or less in consideration of the dispersion stability and aging stability of the silicon oxide-coated zinc oxide.

When the amount of water is adjusted to be in the above-described range, it is possible to obtain a water-based composition including a silicon oxide-coated zinc oxide in which, even in a case in which the composition is used singly or is mixed into a cosmetic, transparency can be sufficiently ensured in a case in which the composition is applied and spread onto the skin.

The water-based composition including a silicon oxide-coated zinc oxide may also be made into a water phase, mixed with an oil phase, and be emulsified, thereby producing an emulsified composition.

[Cosmetic]

A cosmetic of the present embodiment includes either or both the above-described silicon oxide-coated zinc oxide and the above-described composition including a silicon oxide-coated zinc oxide in a base.

In a case in which the silicon oxide-coated zinc oxide is used for an ultraviolet ray-screening use, the average particle diameter of the silicon oxide-coated zinc oxide is preferably in a range of more than 50 nm and 2, 000 nm or less, more preferably in a range of 100 nm or more and 500 nm or less, and still more preferably in a range of 200 nm or more and 300 nm or less.

In addition, even in a case in which the composition including a silicon oxide-coated zinc oxide is used in ultraviolet ray-screening use, the average particle diameter of the silicon oxide-coated zinc oxide included in the composition including a silicon oxide-coated zinc oxide which is used is preferably in a range of more than 50 nm and 2,000 µm or less, more preferably in a range of 100 nm or more and 500 nm or less, and still more preferably in a range of 200 nm or more and 300 nm or less.

The average dispersed-particle diameter of this cosmetic is preferably in a range of 60 nm or more and 10 µm or less, more preferably in a range of 80 nm or more and 7 µm or less, and still more preferably in a range of 100 nm or more and 5 µm or less.

The content rate of the silicon oxide-coated zinc oxide included in the cosmetic for which either or both the above-described silicon oxide-coated zinc oxide and the above-described composition including a silicon oxide-coated zinc oxide are used may be appropriately adjusted, and the content rate thereof is preferably in a range of 1% by mass or more and 60% by mass or less in relation to the mass of the entire cosmetic. When the content of the silicon oxide-coated zinc oxide is in the above-described range, transparency can be sufficiently ensured, and furthermore, a cosmetic having no rough feeling and the like and providing an excellent feeling during use can be obtained.

The cosmetic of the present embodiment may include additives and the like which are generally used for cosmetics such as organic ultraviolet ray-screening agents, inorganic ultraviolet ray-screening agents, and whitening agents as long as the effects of the present invention are not impaired.

Examples of the organic ultraviolet ray-screening agents include anthranilates, cinnamic acid derivatives, salicylic acid derivatives, camphor derivatives, benzophenone derivatives, ββ'-diphenylacrylate derivatives, benzotriazole derivatives, benzalmalonate derivatives, benzimidazole derivatives, imidazolines, bisbenzoazolyl derivatives, p-amino benzoic acid (PABA) derivatives, and methylene bis(hydroxyphenyl benzotriazole) derivatives, and it is possible to selectively use one or more selected from the above-described group.

In addition, examples of the inorganic ultraviolet ray-screening agents include oxides other than zinc oxide, for example, titanium oxide and cerium oxide, and it is possible to selectively use one or more selected from the above-described group.

The cosmetic can be obtained by blending either or both the silicon oxide-coated zinc oxide and the composition including a silicon oxide-coated zinc oxide into a base such as an emulsion, a cream, a foundation, a lipstick, rouge, or eyeshadow as in the related art.

Furthermore, it is possible to obtain a water-based cosmetic having excellent ultraviolet ray-screening performance, transparent feeling, and feeling during use by blending either or both the silicon oxide-coated zinc oxide and the composition including a silicon oxide-coated zinc oxide into a water-based cosmetic such as a facial lotion or a sunscreen gel for which formulation is difficult in the related art.

Furthermore, when this cosmetic is used as a component of a cosmetic product, it is possible to provide a variety of cosmetic products having excellent ultraviolet ray-screening performance, transparent feeling, and feeling during use such as a skincare cosmetic product, a makeup cosmetic product, and a body care cosmetic product. Particularly, the cosmetic is particularly preferable for the sun-screening and the like of a body care cosmetic product requiring ultraviolet ray-screening performance.

As described above, according to the silicon oxide-coated zinc oxide of the present embodiment, when the surfaces of zinc oxide particles are coated with a silicon oxide coat, the average particle diameter of the zinc oxide particles is set in a range of more than 50 nm and 500 nm or less, and furthermore, when the abundance ratio of silicon in the silicon oxide coat in a $Q^3$ environment is indicated by $Q^3$, and the abundance ratio in a $Q^4$ environment is indicated by $Q^4$, $Q^3+Q^4>0.6$ and $Q^4/(Q^3+0.5$ are satisfied, it is possible to suppress the elution of zinc ions from the zinc oxide particles to the outside due to the dense silicon oxide coat that coats the zinc oxide particles. Therefore, in a case in which the silicon oxide-coated zinc oxide is applied to a cosmetic, it is possible to suppress the degradation of performance as cosmetics, discoloration, a change in the viscosity, and the like which are caused by the elution of zinc ions.

According to the method for producing the silicon oxide-coated zinc oxide of the present embodiment, since the zinc oxide suspension production step of producing a zinc oxide suspension by suspending zinc oxide particles in a solvent, the reaction step of adding any one or more of alkoxysilanes and oligomers of alkoxysilanes which are decamer oligomers or smaller, a catalyst, and water to the zinc oxide suspension and causing a reaction, and the thermal treatment step of thermally treating the obtained reaction product at a temperature in a range of 150° C. or higher and lower than 600° C. are provided, it is possible to produce a silicon oxide-coated zinc oxide capable of suppressing the elution of zinc ions from the zinc oxide particles.

According to the composition including a silicon oxide-coated zinc oxide of the present embodiment, since the composition includes the silicon oxide-coated zinc oxide of the present embodiment and a solvent, it is possible to suppress the elution of a zinc element included in the silicon oxide-coated zinc oxide in a zinc ion form to the outside. Therefore, it is possible to suppress the degradation of performance as compositions, discoloration, a change in the viscosity, and the like which are caused by the elution of zinc ions.

In the composition including a silicon oxide-coated zinc oxide, since the elution of zinc ions is suppressed, the composition including a silicon oxide-coated zinc oxide can be preferably used for cosmetics such as water-based dispersion bodies, oil-in-water (O/W) type dispersion bodies, water-in-oil (W/O) type dispersion bodies, and multilayer (W/O/W or O/W/O) type dispersion bodies, particularly for sun screening. In addition, in a case in which the composition including a silicon oxide-coated zinc oxide is applied to a resin film such as polyester or polyamide, it is also possible to preferably use the composition including a silicon oxide-coated zinc oxide as an ultraviolet ray-screening agent for resin films.

Furthermore, since it is possible to mix the composition including a silicon oxide-coated zinc oxide with a carbomer or an aqueous solution of a carbomer, it is possible to provide a water-soluble composition or a non-water-soluble composition having an excellent feeling during use.

According to the cosmetic of the present embodiment, since the cosmetic includes either or both the silicon oxide-coated zinc oxide of the present embodiment and the composition including a silicon oxide-coated zinc oxide of the present embodiment in a base, it is possible to suppress the elution of zinc ions to the outside. Therefore, it is possible to suppress the degradation of performance as cosmetics, discoloration, a change in the viscosity, and the like which are caused by the elution of zinc ions.

[Second embodiment of the present invention]

Hereinafter, a second embodiment of the present invention will be described. In some cases, the common content of the second embodiment with the first embodiment will not be described.

[Silicon oxide-coated zinc oxide]

A silicon oxide-coated zinc oxide of a second embodiment of the present invention is a silicon oxide-coated zinc oxide formed by coating the surfaces of zinc oxide particles with a silicon oxide coat, in which the average particle diameter of the zinc oxide particles is in a range of more than 50 nm and 500 nm or less, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and the decomposition ratio of Brilliant Blue generated by the photocatalytic activity of the zinc oxide particles is 3% or less.

The content rate of the zinc oxide particles in the silicon oxide-coated zinc oxide is the same as that according to the first embodiment.

The average particle diameter of the silicon oxide-coated zinc oxide is the same as that according to the first embodiment.

When the silicon oxide-coated zinc oxide is immersed in an aqueous solution having a hydrogen-ion exponent (pH) of 5 for one hour so that the content thereof reaches 0.05% by mass, the elution ratio of zinc being eluted into this aqueous solution is preferably 20% by mass or less, more preferably 10% by mass or less, and still more preferably 5% by mass or less.

Here, the reason for setting the elution ratio of zinc to 20% by mass or less is that, when the elution ratio of zinc exceeds 20 mass o, the stability of the silicon oxide-coated zinc oxide degrades, in a case in which the silicon oxide-coated zinc oxide is applied to a cosmetic, zinc ions being eluted react with a water-soluble macromolecule or the like such as an organic ultraviolet ray-screening agent or a viscosity improver, and the degradation of performance as cosmetics, discoloration, a change in the viscosity, and the like are caused, which is not preferable.

In this silicon oxide-coated zinc oxide, the decomposition ratio of Brilliant Blue generated by the photocatalytic activity of the zinc oxide particles is preferably 3% or less, more preferably 2% or less, and still more preferably 1% or less.

Here, the reason for setting the decomposition ratio of Brilliant Blue generated by the photocatalytic activity of the zinc oxide particles to 3% or less is that, when the decomposition ratio of Brilliant Blue is 3% or less, the photocatalytic activity of the zinc oxide particles is suppressed, and thus the uniformity of the silicon oxide coat that coats the zinc oxide particles also increases.

Meanwhile, in a case in which the decomposition ratio of Brilliant Blue exceeds 3%, the photocatalytic activity of the zinc oxide particles is not suppressed, and thus the surfaces of the zinc oxide particles are more partially covered with the silicon oxide coat, and the uniformity of the silicon oxide coat becomes poor.

The method for measuring the decomposition ratio of Brilliant Blue is as described below.

First, an aqueous solution of Brilliant Blue in which the content rate of Brilliant Blue is prepared to a predetermined content rate (for example, 5 ppm) is produced, a predetermined amount is sampled from the aqueous solution of Brilliant Blue into a screw pipe, the silicon oxide-coated zinc oxide that amounts to 1% by mass of the mass of the liquid in terms of zinc oxide is injected into the sampled aqueous solution of Brilliant Blue and is ultrasonically dispersed, thereby preparing a suspension. Next, this suspension is irradiated with ultraviolet rays having a predetermined wavelength from a predetermined distance (for example, 10 cm) for a predetermined time (for example, six hours).

As the ultraviolet irradiation lamp, it is possible to use, for example, a bactericidal lamp GL20 (wavelength: 253.7 nm, ultraviolet output: 7.5 W, manufactured by Toshiba Corporation).

Next, the supernatant liquid is sampled from the suspension irradiated with the ultraviolet rays, the respective absorption spectra of the aqueous solution of Brilliant Blue and the supernatant liquid are measured by means of the atomic absorption spectroscopy, and the decomposition ratio D of Brilliant Blue is computed from Expression (1) below using the measurement values.

$$D=(A0-A1)/A0 \quad (1)$$

(Here, AO represents the absorbance of the aqueous solution of Brilliant Blue (5 ppm) at the absorption peak wavelength (630nm) of the absorption spectrum, and A1 represents the absorbance of the supernatant liquid at the absorption peak wavelength of the absorption spectrum.)

Here, as a specific example of the method for measuring the decomposition ratio of Brilliant Blue, the decomposition ratio of Brilliant Blue in zinc oxide (with an average particle diameter of 35 nm; manufactured by Sumitomo Osaka Cement Co., Ltd.) was measured and was found to be 90%. From this result, it is found that, when zinc oxide is photocatalytically active, the decomposition ratio of Brilliant Blue increases.

The silicon oxide-coated zinc oxide may have the surface that is further surface-treated with the silicone resin. This point is the same as in the first embodiment. The surface treatment using the silicone resin is the same as that according to the first embodiment.

The silicone resin used in the surface treatment is the same as in the first embodiment.

In a case in which the surface of the silicon oxide-coated zinc oxide is further surface-treated with the silicone resin, the amount of the surface treatment of the silicone resin in the surface treatment is the same as in the first embodiment.

Hereinafter, individual constitutional elements of the silicon oxide-coated zinc oxide of the present embodiment will be described in detail.

"Zinc oxide particles"

The zinc oxide particles are the same as those according to the first embodiment.

"Silicon oxide coat"

The silicon oxide coat is not particularly limited as long as the silicon oxide coat has a high degree of condensation so that "when the abundance ratio of silicon in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$", which will be described below, are satisfied and has a high uniformity so that the decomposition ratio of Brilliant Blue generated by the photocatalytic activity of the zinc oxide particles reaches 3% or less. The degree of condensation of silicon oxide is the same as that according to the first embodiment.

The uniformity of the silicon oxide coat can be evaluated using the above-described decomposition ratio of Brilliant Blue generated by the photocatalytic activity of the zinc oxide particles.

Here, when the decomposition ratio of Brilliant Blue is 3% or less, the photocatalytic activity of the zinc oxide particles is suppressed, and thus the uniformity of the silicon oxide coat that covers the zinc oxide particles increases.

On the other hand, in a case in which the decomposition ratio of Brilliant Blue exceeds 3%, the photocatalytic activity of the zinc oxide particles is not suppressed, and thus the surfaces of the zinc oxide particles are partially covered with the silicon oxide coat, and the uniformity of the silicon oxide coat becomes poor.

[Method for producing silicon oxide-coated zinc oxide]

A method for producing the silicon oxide-coated zinc oxide of the present embodiment is a method including a surface-modified zinc oxide suspension production step of producing a surface-modified zinc oxide suspension by suspending surface-modified zinc oxide in a solvent, a reaction step of adding any one or more of alkoxysilanes and oligomers of alkoxysilanes which are decamer oligomers or smaller, a catalyst, and water to the surface-modified zinc oxide suspension and causing a reaction, and a thermal treatment step of thermally treating the obtained reaction product at a temperature in a range of 150° C. or higher and lower than 600° C.

Here, the surface-modified zinc oxide refers to a zinc oxide coated with a flexible silicon oxide layer which is capable of easily coating zinc oxide particles in a uniform manner.

The flexible silicon oxide layer maybe a composite oxide of silicon oxide and a metal oxide including 20% by mass or less of a metal oxide such as aluminum oxide or titanium oxide in terms of the oxide.

The surface-modified zinc oxide used herein can be produced as described below.

1% by mass or more and 45% by mass or less of a silicon oxide layer in relation to zinc oxide particles in terms of silicon oxide is formed on the surfaces of the zinc oxide particles having an average particle diameter in a range of more than 50 nm to 500 nm or less using a water-based solution of a silicate of alkaline metal, thereby producing a surface-modified zinc oxide.

Here, the water-based solution of a silicate of alkaline metal refers to a water-based solution in which the silicate of alkaline metal is dissolved in a water-based solvent, and the water-based solvent refers to a solvent including 50% by mass or more of water.

There is no particular limitation regarding solvents other than water, but a polar solvent such as a water-soluble monovalent or polyvalent alcohol is preferred in consideration of the compatibility with water.

There is no particular limitation regarding the silicate of alkaline metal, and it is possible to use a mixture of one or more selected from the group consisting of sodium orthosilicate salts, potassium orthosilicate salts, sodium metasilicate salts, potassium metasilicate salts, and silicate of soda.

Here, first, the amount of the water-based solution of a silicate of alkaline metal is prepared such that 1% by mass or more and 45% by mass or less of a silicon oxide layer in relation to zinc oxide particles in terms of silicon oxide can be generated, zinc oxide particles having an average particle diameter in a range of more than 50 nm and 500 nm or less are added to the water-based solution of a silicate of alkaline metal, and the components are stirred together, thereby producing a suspension including zinc oxide particles.

When a water-soluble compound of aluminum or titanium such as sodium aluminate, aluminum nitrate, aluminum sulfate, or titanyl sulfate is made to coexist in the water-based solution of a silicate of alkaline metal, it is possible to add aluminum oxide, titanium oxide, or the like to the silicon oxide layer.

Next, an acid such as hydrochloric acid is added to the suspension including zinc oxide particles so as to adjust the hydrogen-ion exponent (pH) of the suspension including zinc oxide particles in a range of 6 or more and 9 or less, and the suspension is left to be still.

The reaction temperature is not particularly limited, but is preferably in a range of 40° C. or higher and 100° C. or lower and more preferably in a range of 50° C. or higher and 70° C. or lower in terms of the relationship with the precipitation rate of silicon oxide.

As a result, silicon oxide is precipitated on the surfaces of the zinc oxide particles included in the suspension, and a surface-modified zinc oxide having a silicon oxide layer formed on the surface is produced.

Next, the suspension is separated into solids and liquids, the obtained solid substance is cleaned with a solvent such as water, and furthermore, moisture is removed for the subsequent steps. There is no particular limitation regarding the method for removing moisture; however, generally, the solid substance is preferably dried at a temperature of 100° C. or higher. In addition, in a case in which moisture is removed at a low temperature of 80° C. or lower, reduced-pressure drying is preferred.

A dried substance obtained by removing moisture as described above maybe further subjected to a thermal treatment step.

"Surface-modified zinc oxide suspension production step"

This is a step of producing the surface-modified zinc oxide suspension by suspending the surface-modified zinc oxide in a solvent.

Here, the solvent that suspends surface-modified zinc oxide is not particularly limited as long as the solvent is capable of suspending surface-modified zinc oxide, and examples thereof include, in addition to water, the solvents exemplified in the first embodiment.

The content rate of the surface-modified zinc oxide in the surface-modified zinc oxide suspension is preferably in a range of 1% by mass or more and 80% by mass or less, more preferably in a range of 20% by mass or more and 70% by mass or less, and still more preferably in a range of 30% by mass or more and 60% by mass or less.

The reasons for setting the content rate of the surface-modified zinc oxide in the surface-modified zinc oxide suspension in a range of 1% by mass or more and 80% by mass or less are as described below. When the content rate of the surface-modified zinc oxide is less than 1% by mass, it is necessary to remove a large amount of the solvent compared with the content of the surface-modified zinc oxide in the suspension, and there is a concern that the costs may increase. On the other hand, when the content rate exceeds 80% by mass, the viscous property of the suspension increases (the suspension becomes more viscous), and thus the dispersion stability of the surface-modified zinc oxide degrades, and there is a concern that the surface-modified zinc oxide may easily sink.

As the method for suspending the surface-modified zinc oxide in the solvent, the surface-modified zinc oxide is suspended in water or an organic solvent using a well-known suspension method in order to prevent the surface-modified zinc oxide from being coated with the silicon oxide coat in an agglomerated state. As the suspension method, for example, a beads mill in which media such as zirconia beads are used, a ball mill, a homogenizer, a disper, a stirrer, or the like is preferably used.

The time necessary for the suspension treatment needs to be a sufficient time for the surface-modified zinc oxide to be uniformly suspended in the solvent.

In this case, a dispersant may be added as necessary.

"Reaction step"

This is a step of adding any one or more of alkoxysilanes and oligomers of alkoxysilanes which are decamer oligomers and smaller, a catalyst, and water to the surface-modified zinc oxide suspension and stirring the components for approximately 30 minutes or longer and 24 hours or less, thereby causing a reaction.

The reason for limiting the component to be added to alkoxysilanes and oligomers of alkoxysilanes which are decamer oligomers and smaller is to obtain a dense silicon oxide coat having a high degree of condensation of silicon oxide.

Here, in a case in which a silicate of alkaline metal or trialkoxysilane is used instead of the alkoxysilane, it is difficult to improve the degree of condensation of silicon oxide in the silicon oxide coat, and a dense silicon oxide coat cannot be obtained, which is not preferable.

In addition, the reasons for limiting the oligomers of alkoxysilanes to decamer oligomers and smaller of alkoxysilanes are that, when the chain length of the oligomer becomes long, the distance between the oligomers is likely to be long, and, in the case of an undecamer oligomer or larger, even when a thermal treatment is carried out after the surface-modified zinc oxide is coated, silicon oxide in the coat does not sufficiently condense, and thus a dense silicon oxide coat cannot be obtained, and there is a concern that a desired elution-suppressing effect may not be obtained.

The alkoxysilane is preferably a tetraalkoxysilane, and the oligomer of an alkoxysilane which is a decamer oligomer or smaller is the same as that according to the first embodiment.

The catalyst is the same as that according to the first embodiment. The reaction temperature is the same as that according to the first embodiment.

As a result, the hydrolysis reaction of one or more of the alkoxysilane and the oligomers of the alkoxysilane which are decamer oligomers or smaller proceeds, and a condensation reaction also proceeds, thereby obtaining a reaction liquid.

The reaction liquid is separated into solids and liquids through normal-pressure filtration, reduced-pressure filtration, pressurization filtration, centrifugal separation, or the like, thereby obtaining a solid-phase reaction product.

"Thermal treatment step"

This is a step of thermally treating the above-described reaction product at a temperature in a range of 150° C. or higher and lower than 600° C. The thermal treatment step is the same as that according to the first embodiment.

Through the above-described steps, the silicon oxide-coated zinc oxide of the present embodiment can be produced.

[Composition including silicon oxide-coated zinc oxide]

A composition including a silicon oxide-coated zinc oxide of the present embodiment includes the above-described silicon oxide-coated zinc oxide and a solvent. Hereinafter, the content is the same as that according to the first embodiment.

Next, as specific examples of the composition including a silicon oxide-coated zinc oxide of the present embodiment, (1) a silicone resin-based composition including a silicon oxide-coated zinc oxide in which silicon oxide-coated zinc oxide is dispersed in a silicone resin which is a water-insoluble dispersion medium and (2) a water-based composition including a silicon oxide-coated zinc oxide in which silicon oxide-coated zinc oxide is dispersed in water will be respectively described.

"Silicone resin-based composition including silicon oxide-coated zinc oxide"

The silicone resin-based composition including a silicon oxide-coated zinc oxide is the same as that according to the first embodiment.

In the present embodiment, silicon oxide-coated zinc oxide that is surface-treated with silicone is more preferably preferred.

Examples of the silicone resin include the silicone resins exemplified in the first embodiment.

The method for producing the silicone resin-based composition including a silicon oxide-coated zinc oxide is the same as that in the first embodiment.

"Water-based composition including silicon oxide-coated zinc oxide"

The water-based composition including a silicon oxide-coated zinc oxide is the same as that according to the first embodiment.

[Cosmetic]

A cosmetic of the present embodiment is the same as that according to the first employment.

As described above, according to the silicon oxide-coated zinc oxide of the present embodiment, the surfaces of zinc oxide particles are coated with a dense silicon oxide coat, the average particle diameter of the zinc oxide particles is set in a range of more than 50 nm and 500 nm or less, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and the decomposition ratio of Brilliant Blue generated by the photocatalytic activity of the zinc oxide particles is set to 3% or less. Therefore, the surfaces of the zinc oxide particles are uniformly covered with a dense silicon oxide coat, and thus it is possible to suppress the elution of zinc ions from the zinc oxide particles to the outside. Therefore, in a case in which the silicon oxide-coated zinc oxide is applied to a cosmetic, it is possible to suppress the degradation of performance as cosmetics, discoloration, a change in the viscosity, and the like which are caused by the elution of zinc ions.

According to the method for producing the silicon oxide-coated zinc oxide of the present embodiment, 1% by mass or more and 45% by mass or less of a silicon oxide layer in relation to zinc oxide particles in terms of silicon oxide is formed on the surfaces of the zinc oxide particles having an average particle diameter in a range of more than 50 nm and 500 nm or less using a water-based solution of a silicate of alkaline metal, thereby producing a surface-modified zinc oxide, next, this surface-modified zinc oxide is suspended in a solvent so as to produce a surface-modified zinc oxide suspension, next, anyone or more of alkoxysilanes and oligomers of alkoxysilanes which are decamer oligomers or smaller, a catalyst, and water are added to and reacted with the surface-modified zinc oxide suspension, and then the obtained reaction product is thermally treated at a temperature in a range of 150° C. or higher and lower than 600° C. Therefore, it is possible to uniformly cover the surfaces of the zinc oxide particles with a dense silicon oxide coat. Therefore, it is possible to produce silicon oxide-coated zinc oxide capable of suppressing the elution of zinc ions from zinc oxide particles.

According to the composition including a silicon oxide-coated zinc oxide of the present embodiment, since the silicon oxide-coated zinc oxide of the present embodiment and a solvent are included, it is possible to suppress the elution of a zinc element in the silicon oxide-coated zinc oxide in a zinc ion form to the outside. Therefore, it is possible to suppress the degradation of performance as compositions, discoloration, a change in viscosity, and the like due to the elution of zinc ions.

In the composition including a silicon oxide-coated zinc oxide, since the elution of zinc ions is suppressed, the composition including a silicon oxide-coated zinc oxide can be preferably used for cosmetics such as water-based dispersion bodies, oil-in-water (O/W) type dispersion bodies, water-in-oil (W/O) type dispersion bodies, and multilayer (W/O/W or O/W/O) type dispersion bodies, particularly for sun screening. In addition, in a case in which the composition including a silicon oxide-coated zinc oxide is applied to a resin film such as polyester or polyamide, it is also possible to preferably use the composition including a silicon oxide-coated zinc oxide as an ultraviolet ray-screening agent for resin films.

Furthermore, since it is possible to mix the composition including a silicon oxide-coated zinc oxide with a carbomer or an aqueous solution of a carbomer, it is possible to provide a water-soluble composition or a non-water-soluble composition having an excellent feeling during use.

According to the cosmetic of the present embodiment, the cosmetic includes either or both the silicon oxide-coated zinc oxide of the present embodiment and the composition including a silicon oxide-coated zinc oxide of the present embodiment in a base. Therefore, it is possible to suppress the elution of a zinc element included in either or both the silicon oxide-coated zinc oxide and the composition including a silicon oxide-coated zinc oxide in a zinc ion form into the base. Therefore, it is possible to suppress the degradation of performance as cosmetics, discoloration, a change in the viscosity, and the like which are caused by the elution of zinc ions.

EXAMPLES

Hereinafter, the present invention will be specifically described using examples and comparative examples, but the present invention is not limited to these examples.

Meanwhile, Examples 1 to 3 and Comparative Examples 1 to 5 correspond to the first embodiment.

A. Silicon oxide-coated zinc oxide

Example 1

Zinc oxide particles (with an average particle diameter of 250 nm; manufactured by Sumitomo Osaka Cement Co., Ltd.) and methanol were mixed together and then were ultrasonically dispersed, thereby preparing a zinc oxide methanol suspension having zinc oxide at a content rate of 20% by mass.

Next, methyl silicate 51 (manufactured by Colcoat Co., Ltd.), methanol, and water were mixed with the zinc oxide methanol suspension so that the total content thereof reached 30% by mass in relation to the zinc oxide particles in the zinc oxide methanol suspension in terms of silicon oxide. Next, 1 N hydrochloric acid was added to this liquid mixture, thereby preparing a liquid mixture.

The content rate of zinc oxide in this liquid mixture was 10% by mass, and the molar ratio between methyl silicate 51, pure water, and hydrochloric acid was 1:10:0.1.

Next, the liquid mixture was heated to 60° C., was held at this temperature for three hours, and was reacted.

After the reaction, solids and liquids were separated by means of centrifugal separation, and the obtained solid-phase reaction product was dried at 120° C., thereby obtaining a product.

Next, the product was thermally treated at 500° C. for two hours, thereby obtaining a silicon oxide-coated zinc oxide of Example 1.

Example 2

A silicon oxide-coated zinc oxide of Example 2 was obtained according to Example 1 except for the fact that the amount of the methyl silicate 51 (manufactured by Colcoat Co., Ltd.) added was set to reach 10% by mass in relation to zinc oxide particles in terms of silicon oxide.

Comparative Example 1

Zinc oxide particles (with an average particle diameter of 250 nm; manufactured by Sumitomo Osaka Cement Co., Ltd.) and water were mixed together and then were ultrasonically dispersed, thereby preparing a water-based suspension of zinc oxide having zinc oxide at a content rate of 20% by mass.

Next, the water-based suspension of zinc oxide was added to an aqueous solution of silicate of soda that amounted to 5% by mass in relation to the mass of the zinc oxide particles in the water-based suspension of zinc oxide in terms of silicon oxide and was strongly stirred, thereby producing a suspension of zinc oxide in the solution of silicate of soda.

Next, the suspension of zinc oxide in the solution of silicate of soda was heated to 60° C., dilute hydrochloric acid was gradually added to this suspension, and the pH was adjusted to fall in a range of 6.5 or more and 7 or less. After that, the liquid mixture was left to be still for two hours, the suspension was separated into solids and liquids, and the obtained solid substance was cleaned with water. This solid substance was thermally treated at 150° C. for 12 hours, thereby obtaining a silicon oxide-coated zinc oxide of Comparative Example 1.

Comparative Example 2

A silicon oxide-coated zinc oxide of Comparative Example 2 was obtained according to Comparative Example 1 except for the fact that the amount of the aqueous solution of silicate of soda add in Comparative Example 1 was set to 15% by mass in relation to the mass of the zinc oxide particles in terms of silicon oxide.

[Evaluation]

The respective silicon oxide-coated zinc oxides of Examples 1 and 2 and Comparative Examples 1 and 2 were evaluated. The evaluation items are as described below.

(1) Infrared spectroscopy (IR)

The IR evaluation of the silicon oxide-coated zinc oxide was carried out using a JASCO FT/IR-670 Plus (manufactured by JASCO Corporation) according to the KBr method. Here, a silicon oxide-coated zinc oxide in which a Si-O-Si expansion and contraction-derived absorption band and a zinc oxide-derived absorption band were respectively observed at 1,000 to 1,200 cm$^{-1}$ and 400 to 600 cm$^{-1}$ was evaluated as "0" and a silicon oxide-coated zinc oxide in which either or both of the above-described absorption bands were not observed was evaluated as "X".

(2) Degree of condensation of silicon oxide

The NMR spectrum of the silicon oxide-coated zinc oxide was measured using solid-state $^{29}$Si MAS-nuclear magnetic resonance (NMR) spectroscopy and the area ratios $Q^0$, $Q^1$, $Q^2$, $Q^3$, and $Q^4$ of signals attributed to individual environments of $Q^0$, $Q^1$, $Q^2$, $Q^3$, and $Q^4$ were computed from the peak area ratios of the NMR spectrum.

(3) Elution ratio of zinc

The silicon oxide-coated zinc oxide was dispersed in a buffer solution with a pH of 5 so that the content thereof reached 0.05% by mass, the solution was stirred for one hour, then, solids and liquids were separated, and the concentration of liquid-phase zinc was measured using an ICP optical emission spectrometry analyzer.

In addition, the ratio of zinc ions (mol) eluted into the liquid phase to the content (mol) of zinc in the silicon oxide-coated zinc oxide was considered as the elution ratio of zinc (%).

The buffer solution with a pH of 5 was produced by mixing 500 ml of an aqueous solution of 0.1 M potassium hydrogen phthalate and 226 ml of an aqueous solution of 0.1 M sodium hydroxide and then adding water so that the total amount reached 1,000 ml.

These evaluation results are shown in Tables 1 and 2.

In addition, the measurement result of the elution ratio of zinc of the zinc oxide particles (with an average particle diameter of 250 nm; manufactured by Sumitomo Osaka Cement Co., Ltd.) that were used in Example 1 is shown in Table 2 as Comparative Example 3.

TABLE 1

| | Silicon oxide coat | | Thermal treatment (° C.) | Average particle diameter (nm) | IR |
|---|---|---|---|---|---|
| | Raw material component | % by mass | | | |
| Example 1 | Methyl silicate 51 | 30 | 500 | 250 | o |
| Example 2 | Methyl silicate 51 | 10 | 500 | 250 | o |
| Comparative Example 1 | Silicate of soda | 5 | 150 | 250 | o |
| Comparative Example 2 | Silicate of soda | 15 | 150 | 250 | o |

TABLE 2

|  | $Q^3 + Q^4$ | $Q^4/(Q^3 + Q^4)$ | Elution ratio of zinc (%) |
|---|---|---|---|
| Example 1 | >0.6 | ≥0.5 | 45 |
| Example 2 | >0.6 | ≥0.5 | 51 |
| Comparative Example 1 | >0.6 | <0.5 | 96 |
| Comparative Example 2 | >0.6 | <0.5 | 86 |
| Comparative Example 3 | — | — | >98 |

According to Table 2, it was confirmed that, in the silicon oxide-coated zinc oxides of Examples 1 and 2, compared with the silicon oxide-coated zinc oxides of Comparative Examples 1 and 2, the value of $Q^3+Q^4$ and the value of $Q^4/(Q^3+Q^4)$, which showed the degree of condensation of silicon oxide, were high, and the elution ratios of zinc were low.

B. Composition including silicon oxide-coated zinc oxide

Example 3

A carbomer Ultrez 10 (manufactured by Nikko Chemicals Co., Ltd.) (1.5 g) was dissolved in pure water, and then an aqueous solution of 10% by mass of sodium hydroxide was added dropwise thereto so as to adjust the pH, thereby producing an aqueous solution of a carbomer containing 1.5% by mass of the carbomer and having a pH of 7.5.

Next, this aqueous solution of a carbomer and a silicon oxide-coated zinc oxide obtained according to Example 1 were mixed together at a mass ratio of 95:5 and then were stirred, thereby obtaining a composition including a silicon oxide-coated zinc oxide of Example 3.

The viscosity of the composition was measured using a viscometer BI I-type viscometer (manufactured by Toki Sangyo Co., Ltd.) under conditions of 20° C. and 30 rpm and was found to be 10.4 Pa·s.

A predetermined amount was sampled from this composition, and this sampled specimen was held at 40° C. using a constant-temperature bath, and the viscosity was measured every predetermined time under conditions of 20° C. and 30 rpm. The changes over time of viscosity are shown in Table 1.

Comparative Example 4

A composition including a zinc oxide of Comparative Example 4 was obtained according to Example 3 except for the fact that the zinc oxide particles (with an average particle diameter of 250 nm; manufactured by Sumitomo Osaka Cement Co., Ltd.) were used instead of a silicon oxide-coated zinc oxide obtained according to Example 1.

The viscosity of the composition was measured according to Example 3 and was found to be 2.4 Pa·s.

Comparative Example 5

A carbomer Ultrez 10 (manufactured by Nikko Chemicals Co., Ltd.) (1.5 g) was dissolved in pure water, and then an aqueous solution of 10% by mass of sodium hydroxide was added dropwise thereto so as to adjust the pH, thereby producing an aqueous solution of a carbomer containing 1.5% by mass of the carbomer and having a pH of 7.5.

Next, this aqueous solution of a carbomer and pure water were mixed together at amass ratio of 95:5, and then were stirred, thereby obtaining an aqueous solution of a carbomer of Comparative Example 5.

Next, the viscosity of this aqueous solution of a carbomer was measured according to Example 3 and was found to be 9.5 Pa·s.

A predetermined amount was sampled from this aqueous solution of a carbomer, this sampled specimen was held at 40° C. using a constant-temperature bath, and the viscosity was measured every predetermined time under conditions of 20° C. and 30 rpm. The changes over time of viscosity are shown in Table 1.

According to the above-described results, it was confirmed that, in the composition including a silicon oxide-coated zinc oxide of Example 3, the elution ratio of zinc was sufficiently suppressed, and, while the viscosity decreased for approximately up to 15 hours from the production of the composition, the viscosity remained constant thereafter, and the decrease in the viscosity was suppressed.

In addition, it was confirmed that the viscosity decreased to a small extent in the beginning due to the change over time; however, after a certain period of time elapsed, the viscosity became almost constant thereafter, and the decrease in the viscosity was suppressed.

On the other hand, it was confirmed that, in the composition of Comparative Example 4, the surface of the zinc oxide was not coated with the silicon oxide coat, and thus the elution ratio of zinc was high, and furthermore, the viscosity decreased immediately after the production of the composition.

In Comparative Example 5, zinc oxide was not included in the aqueous solution of a carbomer, and thus the aqueous solution of a carbomer was not affected by the heating and holding at 40° C., and the viscosity was constant at approximately 10 Pa·s.

Next, Examples 4 to 8 and Comparative Examples 6 to 10 according to the second embodiment will be described.

Here, (1) the silicon oxide-coated zinc oxide and (2) the composition including a silicon oxide-coated zinc oxide will be respectively described using examples and comparative examples.

(1) Silicon oxide-coated zinc oxide

Example 4

Zinc oxide particles (with an average particle diameter of 250 nm; manufactured by Sumitomo Osaka Cement Co., Ltd.) and water were mixed together and then were ultrasonically dispersed, thereby preparing a zinc oxide water-based suspension having zinc oxide at a content rate of 20% by mass.

Next, this zinc oxide water-based suspension was added to an aqueous solution of silicate of soda that amounted to 15% by mass in relation to the mass of the zinc oxide particles in the zinc oxide water-based suspension in terms of silicon oxide and was strongly stirred, thereby producing a suspension.

Next, this suspension was heated to 60° C., then, dilute hydrochloric acid was gradually added to the suspension, and the pH was adjusted to fall in a range of 6.5 or more and 7 or less. After that, the liquid mixture was left to be still for two hours, the suspension was separated into solids and liquids, and the obtained solid substance was cleaned with water. This solid substance was thermally treated at 150° C. for one hour, thereby obtaining a surface-modified zinc oxide A.

Next, this surface-modified zinc oxide A and 2-propanol were mixed together and then were ultrasonically dispersed, thereby preparing a surface-modified zinc oxide A2-propanol suspension in which the content rate of the surface-modified zinc oxide A was 10% by mass.

Next, this surface-modified zinc oxide A2-propanol suspension was heated to 60° C., ammonia water and water were added thereto under stirring, and the pH was adjusted so as to fall in a range of 10 or more and 11 or less. Furthermore, a solution of tetramethoxysilane (TMOS) 2-propanol was slowly added dropwise thereto, and the components were continuously stirred for six hours and were reacted with each other.

The amount of the tetramethoxysilane added dropwise was 15% by mass in relation to zinc oxide in terms of silicon oxide. In addition, the content of water was 120% by mass of the tetramethoxysilane.

After the reaction, solids and liquids were separated by means of centrifugal separation, and the obtained solid-phase reaction product was thermally treated at 150° C. for 12 hours, thereby obtaining a silicon oxide-coated zinc oxide A of Example 4.

Example 5

A silicon oxide-coated zinc oxide A obtained according to Example 4 was thermally treated at 500° C. for two hours, thereby obtaining a silicon oxide-coated zinc oxide B of Example 5.

Example 6

A surface-modified zinc oxide C of Example 6 was obtained in the same manner as in Example 4 except for the fact that the zinc oxide water-based suspension of Example 4 was added to the aqueous solution of silicate of soda that amounted to 5% by mass in relation to the mass of the zinc oxide particles in the zinc oxide water-based suspension in terms of silicon oxide.

Next, this surface-modified zinc oxide C and 2-propanol were mixed together and then were ultrasonically dispersed, thereby preparing a surface-modified zinc oxide C2-propanol suspension in which the content rate of the surface-modified zinc oxide C was 10% by mass.

Next, this surface-modified zinc oxide C2-propanol suspension was heated to 60° C., ammonia water and water were added thereto under stirring, and the pH was adjusted so as to fall in a range of 10 or more and 11 or less. Furthermore, a solution of tetramethoxysilane (TMOS) 2-propanol was slowly added dropwise thereto, and the components were continuously stirred for six hours and were reacted with each other.

The amount of the tetramethoxysilane added dropwise was 5% by mass in relation to zinc oxide in terms of silicon oxide. In addition, the content of water was 120% by mass of the tetramethoxysilane.

After the reaction, solids and liquids were separated by means of centrifugal separation, and the obtained solid-phase reaction product was thermally treated at 150° C. for 12 hours, thereby obtaining a silicon oxide-coated zinc oxide C of Example 6.

Example 7

A silicon oxide-coated zinc oxide C obtained according to Example 6 was thermally treated at 500° C. for two hours, thereby obtaining a silicon oxide-coated zinc oxide D of Example 7.

Comparative Example 6

Zinc oxide particles (with an average particle diameter of 250 nm; manufactured by Sumitomo Osaka Cement Co., Ltd.) and water were mixed together and then were ultrasonically dispersed, thereby preparing a zinc oxide water-based suspension having zinc oxide at a content rate of 20% by mass.

Next, this zinc oxide water-based suspension was added to an aqueous solution of silicate of soda that amounted to 15% by mass in relation to the mass of the zinc oxide particles in the zinc oxide water-based suspension in terms of silicon oxide and was strongly stirred, thereby producing a suspension.

Next, this suspension was heated to 60° C., then, dilute hydrochloric acid was gradually added to this suspension, and the pH was adjusted to fall in a range of 6.5 or more and 7 or less. After that, the liquid mixture was left to be still for two hours, the suspension was separated into solids and liquids, and the obtained solid substance was cleaned with water. This solid substance was thermally treated at 150° C. for 12 hours, thereby obtaining a surface-modified zinc oxide E of Comparative Example 6.

Comparative Example 7

A surface-modified zinc oxide E obtained according to Comparative Example 6 was thermally treated at 500° C. for two hours, thereby obtaining a surface-modified zinc oxide F of Comparative Example 7.

[Evaluation]

The respective silicon oxide-coated zinc oxides of Examples 4 to 7 and surface-modified zinc oxides of Comparative Examples 6 and 7 were respectively evaluated. The evaluation items are as described below.

(1) Average particle diameter

The silicon oxide-coated zinc oxide (or the surface-modified zinc oxide) was observed using a transmission electron microscope (TEM), 200 particles were selected, the longest straight line portions (maximum length diameters) of the respective silicon oxide-coated zinc oxide (or surface-modified zinc oxide) particles were measured, and these measurement values were weight-averaged, thereby computing the average particle diameter.

(2) Infrared spectroscopy (IR)

The IR evaluation of the silicon oxide-coated zinc oxide (or the surface-modified zinc oxide) was carried out using a JASCO FT/IR-670 Plus (manufactured by JASCO Corporation) according to the KBr method. Here, a silicon oxide-coated zinc oxide in which a Si-O-Si expansion and contraction-derived absorption band and a zinc oxide-derived absorption band were respectively observed at 1,000 to 1,200 $cm^{-1}$ and 400 to 600 $cm^{-1}$ was evaluated as "O" and a silicon oxide-coated zinc oxide in which either or both of the above-described absorption bands were not observed was evaluated as "X".

(3) Degree of condensation of silicon oxide

The NMR spectrum of the silicon oxide-coated zinc oxide (or the surface-modified zinc oxide) was measured using solid-state $^{29}Si$ MAS-nuclear magnetic resonance (NMR) spectroscopy, the area ratios $Q^0$, $Q^1$, $Q^2$, $Q^3$, and $Q^4$ of signals attributed to individual environments of $Q^0$, $Q^1$, $Q^2$, $Q^3$, and $Q^4$ were computed from the peak area ratios of the NMR spectrum, and then, when the abundance ratio of silicon in the silicon oxide coat (or the surface-modified coat) in a $Q^3$ environment was indicated by $Q^3$, and the abundance ratio in a $Q^4$ environment was indicated by $Q^4$, the value of $Q^3+Q^4$ and the value of $Q^4/(Q^3+Q^4)$ were computed.

Here, waveform separation was carried out on the measurement data $Q^d$ so that the measurement data was fitted to actual NMR spectrum measurement data $Q^d$, thereby producing $Q^2$, $Q^3$, and $Q^4$.

Figure 2:
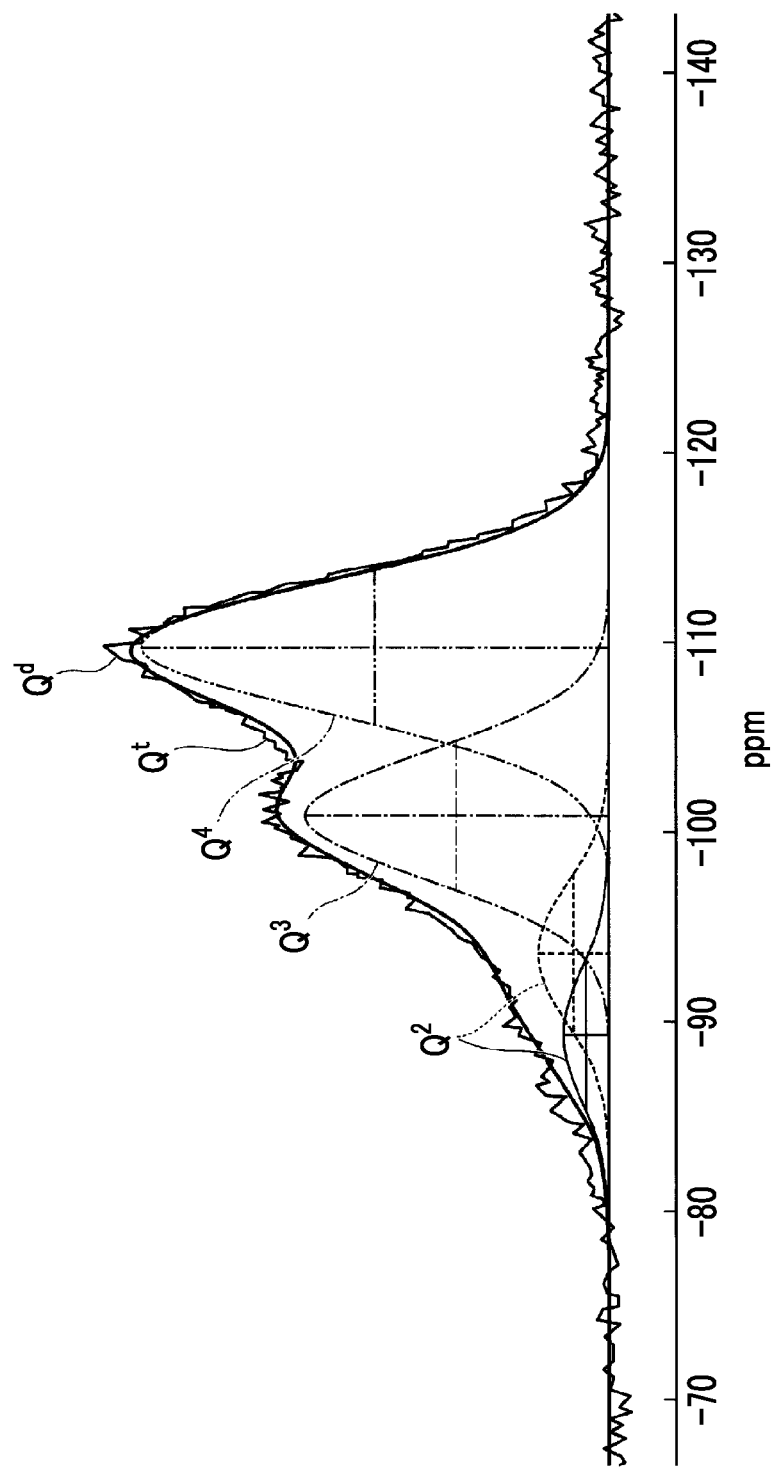
FIG. 2 is a diagram illustrating an NMR spectrum of the silicon oxide-coated zinc oxide of Example 5 of the present invention.

Furthermore, as an example of the NMR spectrum, the NMR spectrum of the silicon oxide-coated zinc oxide of Example 5 is illustrated in FIG. 2.

In FIG. 2, the NMR spectrum indicated by $Q^t$ in the drawing is a spectrum obtained by summing the waveform-separated NMR spectra $Q^2$, $Q^3$, and $Q^4$ and is indicated by a smooth curve. This NMR spectrum indicated by Qt well coincides with the measurement data $Q^d$ including actual noise.

puted from Expression (1) described above using the measurement values.

The raw material components and the like and the evaluation results of the respective silicon oxide-coated zinc oxides of Examples 4 to 7 and the respective surface-modified zinc oxides of Comparative Examples 6 and 7 are shown in Tables 3 and 4.

In addition, the measurement results of the elution ratio of zinc and the decomposition ratio of Brilliant Blue of the zinc oxide particles (with an average particle diameter of 250 nm; manufactured by Sumitomo Osaka Cement Co., Ltd.) used in Example 4 are shown in Table 4 as Comparative Example 8.

TABLE 3

| | Surface-modified | | Silicon oxide coat | | | Average | |
|---|---|---|---|---|---|---|---|
| | Raw material component | % by mass | Raw material component | % by mass | Thermal treatment (° C.) | particle diameter (nm) | IR |
| Example 4 | Silicate of soda | 15 | TMOS | 15 | 150 | 250 | ○ |
| Example 5 | Silicate of soda | 15 | TMOS | 15 | 150/500 | 250 | ○ |
| Example 6 | Silicate of soda | 5 | TMOS | 5 | 150 | 250 | ○ |
| Example 7 | Silicate of soda | 5 | TMOS | 5 | 150/500 | 250 | ○ |
| Comparative Example 6 | Silicate of soda | 15 | — | — | 150 | 250 | ○ |
| Comparative Example 7 | Silicate of soda | 15 | — | — | 150/500 | 250 | ○ |

(4) Elution ratio of zinc

The silicon oxide-coated zinc oxide (or the surface-modified zinc oxide) was injected into a buffer solution with a pH of 5 so that the content thereof reached 0.05% by mass, then, the solution was stirred for one hour so as to disperse the zinc oxide, then, solids and liquids were separated, and the concentration of liquid-phase zinc was measured using an ICP optical emission spectrometry analyzer.

In addition, the ratio of zinc ions (mol) eluted into the liquid phase to the content (mol) of zinc in the silicon oxide-coated zinc oxide (or the surface-modified zinc oxide) was considered as the elution ratio of zinc (%).

The buffer solution with a pH of 5 was produced by mixing 500 ml of an aqueous solution of 0.1 M potassium hydrogen phthalate and 226 ml of an aqueous solution of 0.1 M sodium hydroxide and then adding water so that the total amount reached 1,000 ml.

(5) Decomposition ratio of Brilliant Blue

An aqueous solution of Brilliant blue in which the content rate of Brilliant Blue was adjusted to 5 ppm was produced, 0.15 g of the silicon oxide-coated zinc oxide (or the surface-modified zinc oxide) in terms of zinc oxide was injected into 15 g of this aqueous solution of Brilliant blue, was ultrasonically dispersed so as to prepare a suspension, the suspension was irradiated from an irradiation distance of 10 cm for six hours using an ultraviolet lamp (having a central wavelength: 254 nm), and then the supernatant liquid was sampled.

Next, the respective absorption spectra of the aqueous solution of Brilliant Blue and the supernatant liquid were measured by means of the atomic absorption spectroscopy, and the decomposition ratio D of Brilliant Blue was com-

TABLE 4

| | $Q^3 + Q^4$ | $Q^4/(Q^3 + Q^4)$ | Elution ratio of zinc (%) | Decomposition ratio of Brilliant Blue (%) |
|---|---|---|---|---|
| Example 4 | >0.6 | ≥0.5 | 12 | <1.0 |
| Example 5 | >0.6 | ≥0.5 | 6 | <1.0 |
| Example 6 | >0.6 | ≥0.5 | 59 | 3.0 |
| Example 7 | >0.6 | ≥0.5 | 25 | 3.0 |
| Comparative Example 6 | >0.6 | <0.5 | 86 | 6.0 |
| Comparative Example 7 | >0.6 | ≥0.5 | 22 | 6.0 |
| Comparative Example 8 | — | — | >98 | 45 |

According to Tables 3 and 4, it was confirmed that, in the silicon oxide-coated zinc oxides of Examples 4 to 7, compared with the surface-modified zinc oxides of Comparative Examples 6 and 8, $Q^3+Q^4≥0.6$ and $Q^4/(Q^3+Q^4)≥0.5$ were satisfied, and the decomposition ratio of Brilliant Blue was set to 3% or less, and thus a dense and uniform silicon oxide coat was formed on the surfaces of the zinc oxide particles, and it was possible to decrease the elution ratio of zinc.

(2) Composition including silicon oxide-coated zinc oxide

Example 8

A carbomer Ultrez 10 (manufactured by Nikko Chemicals Co., Ltd.) (1.5 g) was dissolved in pure water, and then an aqueous solution of 10% by mass of sodium hydroxide was added dropwise thereto so as to adjust the pH, thereby producing an aqueous solution of a carbomer which included 1.5% by mass of the carbomer and had a pH of 7.5.

Next, this aqueous solution of a carbomer and the silicon oxide-coated zinc oxide B obtained according to Example 5 were mixed together at a mass ratio of 95:5, and then were stirred, thereby obtaining a composition including a silicon oxide-coated zinc oxide of Example 8.

The viscosity of the composition was measured using a viscometer BI I-type viscometer (manufactured by Toki Sangyo Co., Ltd.) under conditions of 20° C. and 30 rpm and was found to be 10.4 Pa·s.

A predetermined amount was sampled from this composition, and this sampled specimen was held at 40° C. using a constant-temperature bath, and the viscosity was measured every predetermined time under conditions of 20° C. and 30 rpm. The measurement results of the viscosity are shown in Table 3.

Comparative Example 9

A composition including zinc oxide of Comparative Example 9 was obtained according to Example 8 except for the fact that zinc oxide particles (with an average particle diameter of 250 nm; manufactured by Sumitomo Osaka Cement Co., Ltd.) were used instead of the silicon oxide-coated zinc oxide obtained according to Example 4.

The viscosity of the composition was measured according to Example 8 and was found to be 2.4 Pa·s.

Comparative Example 10

A carbomer Ultrez 10 (manufactured by Nikko Chemicals Co., Ltd.) (1.5 g) was dissolved in pure water, and then an aqueous solution of 10% by mass of sodium hydroxide was added dropwise thereto so as to adjust the pH, thereby producing an aqueous solution of a carbomer which included 1.5% by mass of the carbomer and had a pH of 7.5.

Next, this aqueous solution of a carbomer and pure water were mixed together at amass ratio of 95:5, and then were stirred, thereby obtaining an aqueous solution of a carbomer of Comparative Example 10.

Next, the viscosity of the aqueous solution of a carbomer was measured according to Example 8 and was found to be 9.5 Pa·s.

Figure 3:
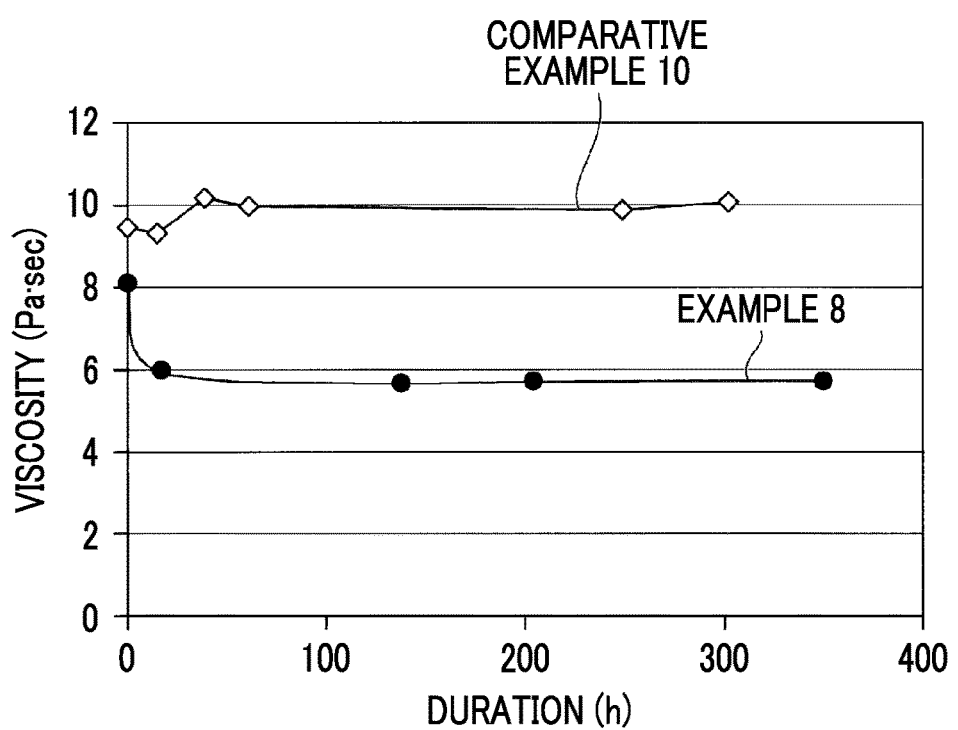
FIG. 3 is a diagram illustrating changes in viscosity over time at 40° C. of a composition including a silicon oxide-coated zinc oxide of Example 8 of the present invention and an aqueous solution of a carbomer of Comparative Example 10 of the present invention.

A predetermined amount was sampled from this aqueous solution of a carbomer, and this sampled specimen was held at 40° C. using a constant-temperature bath, and the viscosity was measured every predetermined time under conditions of 20° C. and 30 rpm. The measurement results for the viscosity are shown in FIG. 3.

According to the above-described results, it was confirmed that, in the composition including a silicon oxide-coated zinc oxide of Example 8, the elution ratio of zinc was sufficiently suppressed, and, while the viscosity decreased for approximately up to 15 hours from the production of the composition, the viscosity remained constant thereafter, and the decrease in the viscosity was suppressed.

In addition, it was confirmed that the viscosity decreased to a small extent in the beginning due to a change over time; however, after a certain period of time elapsed, the viscosity became almost constant thereafter, and the decrease in the viscosity was suppressed.

Meanwhile, it was confirmed that, in the composition of Comparative Example 9, the surface of the zinc oxide was not coated with the silicon oxide coat, and thus the elution ratio of zinc was high, and furthermore, the viscosity decreased immediately after the production of the composition.

In Comparative Example 10, zinc oxide was not included in the aqueous solution of a carbomer, and thus the aqueous solution of a carbomer was not affected by the heating and holding at 40° C., and the viscosity was constant at approximately 10 Pa·s.

INDUSTRIAL APPLICABILITY

In the silicon oxide-coated zinc oxide of the present invention, the average particle diameter of the zinc oxide particles in the silicon oxide-coated zinc oxide formed by coating the surfaces of zinc oxide particles with a silicon oxide coat is set in a range of more than 50 nm and 500 nm or less, and, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied. Therefore, it is possible to suppress the elution of zinc ions from the zinc oxide particles to the outside, and, in a case in which the silicon oxide-coated zinc oxide is applied to a cosmetic, it is possible to suppress the degradation of performance as cosmetics, discoloration, a change in the viscosity, and the like which are caused by the elution of zinc ions. As a result, the silicon oxide-coated zinc oxide can be applied to cosmetic products which require ultraviolet ray-screening performance and have excellent feeling during use, and, even in a case in which the silicon oxide-coated zinc oxide is used in fields other than cosmetic products, there is a wide range of choice for dispersants or resins, and it is possible to increase the degree of freedom in design and formulation of paints and the like. Therefore, the silicon oxide-coated zinc oxide has a large industrial value.

In the silicon oxide-coated zinc oxide of the present invention, the average particle diameter of the zinc oxide particles in the silicon oxide-coated zinc oxide formed by coating the surfaces of zinc oxide particles with a dense silicon oxide coat is set in a range of more than 50 nm and 500 nm or less, and, furthermore, when the abundance ratio of silicon in the silicon oxide coat in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and, furthermore, the decomposition ratio of Brilliant Blue generated by the photocatalytic activity of the zinc oxide particles is set to 3% or less. Therefore, the surfaces of the zinc oxide particles are uniformly covered with a dense silicon oxide coat, and thus it is possible to suppress the elution of zinc ions from the zinc oxide particles to the outside. Therefore, in a case in which the silicon oxide-coated zinc oxide is applied to a cosmetic, it is possible to suppress the degradation of performance as cosmetics, discoloration, a change in the viscosity, and the like which are caused by the elution of zinc ions. As a result, the silicon oxide-coated zinc oxide can be reliably applied to cosmetic products which require ultraviolet ray-screening performance and have excellent feeling during use, and, even in a case in which the silicon oxide-coated zinc oxide is used in fields other than cosmetic products, there is a wide range of choice for dispersants or resins, and it is possible to increase the degree of freedom in design and formulation of paints and the like. Therefore, the silicon oxide-coated zinc oxide has a large industrial value.

The invention claimed is:
1. A silicon oxide-coated zinc oxide, comprising:
  zinc oxide particles having an average particle diameter in a range of more than 100 nm to 500 nm, and
  a silicon oxide coating on the surface of the zinc oxide particles; in which, when an abundance ratio of silicon in the silicon oxide coating in a $Q^3$ environment is indicated by $Q^3$, and an abundance ratio in a $Q^4$ environment is indicated by $Q^4$, $Q^3+Q^4 \geq 0.6$ and $Q^4/(Q^3+Q^4) \geq 0.5$.

2. The silicon oxide-coated zinc oxide according to claim 1,
wherein the zinc oxide particles has a decomposition ratio of Brilliant Blue generated by a photocatalytic activity of the zinc oxide particles of 3% or less.

3. The silicon oxide-coated zinc oxide according to claim 1,
wherein a content rate of the zinc oxide particles is in a range of 50% by mass to 99% by mass.

4. The silicon oxide-coated zinc oxide according to claim 1,
wherein, when the silicon oxide-coated zinc oxide is immersed in an aqueous solution having a hydrogen-ion exponent of 5 so that the content thereof reaches 0.05% by mass, an elution ratio of zinc being eluted in the aqueous solution is 60% by mass or less.

5. The silicon oxide-coated zinc oxide according to claim 4, wherein the elution ratio of zinc being eluted in the aqueous solution is 20% by mass or less.

6. A composition comprising:
silicon oxide-coated zinc oxide comprising zinc oxide particles having an average particle diameter in a range of more than 100 nm to 500 nm, and a silicon oxide coating on the surface of the zinc oxide particles in which, when an abundance ratio of silicon in the silicon oxide coating in a $Q^3$ environment is indicated by $Q^3$, and an abundance ratio in a $Q^4$ environment is indicated by $Q^4$, $Q^3+Q^4 \geq 0.6$ and $Q^4/(Q^3+Q^4) \geq 0.5$; and
a solvent.

7. A cosmetic composition comprising: the silicon oxide-coated zinc oxide according to claim 1, and a cosmetic base.

8. The cosmetic composition according to claim 7, further comprising a solvent.

9. The silicon oxide-coated zinc oxide according to claim 1, wherein the zinc oxide particles have an average particle diameter in a range of 200 nm to 500 nm.

* * * * *